(12) United States Patent
Kakizuka et al.

(10) Patent No.: US 9,782,420 B2
(45) Date of Patent: Oct. 10, 2017

(54) METHOD FOR TREATING EYE DISEASES

(71) Applicant: Kyoto University, Kyoto (JP)

(72) Inventors: Akira Kakizuka, Takatsuki (JP);
Hanako Ikeda, Kyoto (JP); Nagahisa Yoshimura, Kyoto (JP); Yuki Muraoka, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 14/768,949

(22) PCT Filed: Feb. 19, 2014

(86) PCT No.: PCT/JP2014/053898
§ 371 (c)(1),
(2) Date: Aug. 19, 2015

(87) PCT Pub. No.: WO2014/129495
PCT Pub. Date: Aug. 28, 2014

(65) Prior Publication Data
US 2016/0000810 A1    Jan. 7, 2016

(30) Foreign Application Priority Data
Feb. 20, 2013   (JP) ................ 2013-031190

(51) Int. Cl.
*A61K 31/655*     (2006.01)
*A61K 31/4418*    (2006.01)
*C07D 213/77*     (2006.01)

(52) U.S. Cl.
CPC ........ *A61K 31/655* (2013.01); *A61K 31/4418* (2013.01); *C07D 213/77* (2013.01)

(58) Field of Classification Search
CPC . A61K 31/644; A61K 31/4418; C07D 213/77
See application file for complete search history.

(56) References Cited

U.S. PATENT DOCUMENTS

| | | |
|---|---|---|
| 2003/0065020 A1 | 4/2003 | Gale et al. |
| 2013/0184241 A1* | 7/2013 | Kakizuka ............. C07C 309/47 514/150 |
| 2014/0148416 A1 | 5/2014 | Kakizuka et al. |

FOREIGN PATENT DOCUMENTS

| | | | |
|---|---|---|---|
| WO | 2012/014994 A1 | 2/2012 | |
| WO | WO 2012/014994 A1 * | 2/2012 | ........... C07C 309/47 |
| WO | 2012/043891 A1 | 4/2012 | |

OTHER PUBLICATIONS

AREDS Report No. 8, "A randomized, Placebo-Controlled, Clinical Trial of High-Dose Supplementation With Vitamins C and E, Beta Carotene, and Zinc for Age-Related Macular Degeneration" Arch Opthalmol, 119(10), p. 1417-1436, 2001.*

International Search Report issued in corresponding International Patent Application No. PCT/JP2014/053898 dated Apr. 28, 2014.
International Preliminary Report on Patentability issued in corresponding International Patent Application No. PCT/JP2014/053898 dated Dec. 2, 2014.
Extended European Search Report issued in corresponding European Patent Application No. 14754749.1 dated Jul. 1, 2016.
Chi et al., "Suppression of Drusen Formation by Compstatin, a Peptide Inhibitor of Complement C3 activation, on Cynomolgus Monkey with Early-Onset Macular Degeneration," Advances in Experimental Medicine and Biology, 703: 127-135 (2010).
Muraoka et al., "Suppression of Drusen by VCP Inhibitors in CCR2 Deficient Mice," Journal of Japanese Ophthalmological Society, 117: 295 (2013).
Merle et al., "Dietary Omega-3 Fatty Acids and the Risk for Age-Related Maculopathy: The Alienor Study," IOVS, 52: 6004-6011 (2011).
Ortak et al., "Expression of p97/VCP and ubiquitin during postnatal development of the degenerating rat retina," Journal of Molecular Histology, 43: 17-25 (2012).
Nat Med. Nov. 2003;9(11):1390-7. An animal model of age-related macular degeneration in senescent Ccl-2- or Ccr-2-deficient mice. Ambati J(1), Anand A, Fernandez S. Sakurai E, Lynn BC, Kuziel WA, Rollins BJ, Ambati BK.
Lee EJ, Kim N, Kang KH, Kim JW. Phosphorylation/inactivation of PTEN by Akt-independent PI3K signaling in retinal pigment epithelium. Biochem Biophys Res Commun. Oct. 22, 2011;414(2):384-9. doi: 10.106/j.bbre.2011.09.083. Epub Sep. 2011.
Chen M, Forrester JV, Xu H. Dysregulation in retinal para-inflammation and age-related retinal degeneration in CCL2 or CCR2 deficient mice. PLoS One.2011;6(8):e22818. doi: 10.1371/journal.pone.0022818. Epub Aug. 5, 2011. PubMed PMID: 21850237.
Swaroop A, Chew EY, Rickman CB, Abecasis GR (2009). Unraveling a multifactorial late-onset disease: From genetic susceptibility to disease mechanisms for age-related macular degeneration. Annu Rev Genomics Human Genet, 10:19-43.
Marmorstein AD, Marmorstein LY. The challenge of modeling macular degeneration in mice. Trends Genet. May 2007;23(5):225-31. Epub Mar. 26, 2007. PubMed PMID:17368622.
Rattner A, Nathans J. Macular degeneration: recent advances and therapeutic opportunities. Nat. Rev Neurosci. Nov. 2006;7(11):860-72. Epub Oct. 11, 2006. Review. PubMed PMID: 17033682.
Jakub Hanus, Chastain Anderson, Shusheng Wang, RPE necroptosis in response to oxidative stress and in AMD, Ageing Research Reviews, vol. 24, Part. B, Nov. 2015, pp. 286-298, ISSN 1568-1638, http://dx.doi.org/10.1016/j.arr.2015.09.002. (http://www.sciencedirect.com/science/article/pii/S1568163715300222).

(Continued)

*Primary Examiner* — Craig Ricci
*Assistant Examiner* — Christopher R Stone
(74) *Attorney, Agent, or Firm* — Morgan, Lewis & Bockius LLP

(57) ABSTRACT

The present invention provides a pharmaceutical composition for removing drusen, suppressing formation of drusen, and/or treating and/or preventing age-related macular degeneration comprising the compound of formula (I) wherein Ra is independently selected from the group consisting of halo, hydroxy, alkyl, halo-substituted alkyl, aryl, halo- or alkyl-substituted aryl, alkoxy, hydroxy- or carboxy-substituted alkoxy, aryloxy, halo- or alkyl-substituted aryloxy, CHO, C(O)-alkyl, C(O)-aryl, C(O)-alkyl-carboxyl, C(O)-alkylene-carboxy ester and cyano, and m is an integer selected from 0 to 4.

20 Claims, 7 Drawing Sheets

(56) References Cited

OTHER PUBLICATIONS

Mark E. Pennesi, Martha Neuringer, Robert J. Courtney, Animal models of age related macular degeneration, Molecular Aspects of Medicine, vol. 33, Issue 4, Aug. 2012, pp. 487-509, ISSN 0098-2997, http://dx.doi.org/10106/j.mam.2012.06.003. (http://www.sciencedirect.com/science/article/pii/S00982997212000635).
S. Khandhadia, V. Cipriani, J.R.W. Yates, A.J. Lotery, Age-related mascular degeneration and the complement system, Immumobiology, vol. 217, Issue 2, Feb. 2012, pp. 127-146. ISSN 0171-2985, http://dx.doi.org/10.1026/j.imbio.2011.07.019. (http://www.sciencedirect.com/science/article/pii/S0171298511001598).
Retinal Neovascular Disorders: Mouse Models for Drug Development Studies. Yetemian, Rosanne M.; Craft, Cheryl M. Edited by LaVail, MM; Ash, JD; Anderson, RE; et al. Retinal Degenerative Diseases, Series Title: Advances in Experimental Medicine and Biology, vol. 723, pp. 253-259, 2012.
Stem cell-based therapeutic applications in retinal degenerative diseases. Huang, Yiming Y. Stem cell reviews, 2011, vol. 7 (2) 434-445, PMID: 20859770, 10.1007/s12015-010-9192-8.
CCL2/CCR2 and CX3CL1/CX3CR1 chemokine axes and their possible involvement in age-related macular degeneration. Journal of Neuroinflammation. 2010, vol. 7, p. 87-93. 7p. DOI: 10.1186/1742-2094-7-87.
The Mouse Retina as an Angiogenesis Model. Andreas Stahl; Kip M. Connor; Przemyslaw Sapieha; Jing Chen; Roberta J. Dennison; Nathan M. Krah; Molly R. Seaward: Keirnan L. Willett; Christopher M. Aderman; Karen I. Guerin; Jing Hua; Chatarina Löfqvist; Ann Hellström; Lois E. H. Smith. Invest. Ophthalmol. Vis. Sci.. 2010; 51(6):2813-2826. doi: 10.1167/iovs.10-5176.
Hema L. Ramkumar, Jun Zhang, Chi-Chao Chan, Retinal ultrastructure of murine models of dry age-related macular degeneration (AMD), Progress in Retinal and Eye Research, vol. 29, Issue 3, May 2010, pp. 169-190, ISN 1350-9462, http://dx.doi.org/10.1016/j.preteyeres.2010.02.002. (http://www.sciencedirect.com/science/article/pii/S1350946210000145).
C. J. Zeiss. Review Paper: Animals as Models of Age-Related Macular Degeneration: An Imperfect Measure of the Truth. Vet Pathol May 2010 47: 396-413, first published on Apr. 9, 2010 doi:10.1177/0300985809359598.
Animal Models for Age-Related Macular Degeneration. Hollyfield, Joe G.; Kuttner-Kondo, Lis. Edited by Pang, IH; Clark, AF. Animal Models for Retinal Diseases, Series Title; Neuromethods, 46, 81-98, 2010.

\* cited by examiner

Control

▲ drusen

Compound 32

▼ drusen

Compound 32  3.5M  9M

Comparison of Electroretinogram amplitudes
of mice at age of 9 months in Experiment 2

Comparison of Electroretinogram amplitudes
of mice at age of 9 months in Experiment 2

METHOD FOR TREATING EYE DISEASES

TECHNICAL FIELD

The present application claims priority to Japanese patent application no. 2013-31190, the content of which is incorporated herein by reference in its entirety.

The present invention provides an agent effective to treat an eye disease, a pharmaceutical composition comprising the agent, a method for preparing a pharmaceutical for treating an eye disease comprising using the agent, use of the agent in manufacture of a pharmaceutical for treating an eye diseases and a method for treating an eye disease comprising administering the agent or the pharmaceutical composition. The treated eye disease may be age-related macular degeneration including exudative age-related macular degeneration and atrophic age-related macular degeneration.

BACKGROUND ART

Age-related macular degeneration is an eye disease with symptoms such as impaired or distorted central vision. It is one of the major causes of blindness in the elderly in developed countries. In the United States, about 15% of the people over 80 years of age were suffering from age-related macular degeneration in 2000. In Japan, in association with the aging society and the westernized food culture, patients of age-related macular degeneration have been increasing in recent years and it has become the fourth most common cause of acquired blindness.

Drusen, a waste product mainly comprising lipid, accumulates under the retinal pigment epithelium of the patients of age-related macular degeneration. Subsequently, in the case of exudative age-related macular degeneration subchoroidal neovascularization occurs, followed by reduced vision due to subretinal hemorrhage or retinal edema. Only vascular regression therapy (intravitreal administration of an anti-VEGF agent or photodynamic therapy) for established neovessels is currently available and effective for treating exudative age-related macular degeneration. Unfortunately, once neovascularization occurs, prognosis is generally poor even if such therapy is applied. For maintaining good vision it is important to suppress progression of the disease at the stage of the drusen formation, but no such therapy is currently available.

In the case of atrophic age-related macular degeneration, following the drusen accumulation chorioretinal atrophy gradually occurs without neovascularization, causing reduced vision. No effective therapy is currently available for atrophic age-related macular degeneration. Sometimes exudative age-related macular degeneration proceeds to atrophic age-related macular degeneration.

Accordingly, removing the drusen and/or suppressing the formation of the drusen is considered to be effective for treating and/or preventing age-related macular degeneration, but no agent having such effect exists.

CITATION LIST

Patent Literature

Patent Literature 1: WO2012/014994
Patent Literature 2: WO2012/043891

Non-Patent Literature

Non-Patent Literature 1: Suppression of drusen formation by compstatin, a peptide inhibitor of complement C3 activation, on cynomolgus monkey with early-onset macular degeneration. Adv Exp Med Biol. 703, 127-35
Non-Patent Literature 2: IOVS 2011, 52, 6004

SUMMARY OF INVENTION

An object of the invention is to provide a pharmaceutical capable of removing drusen, which are precursor lesions of age-related macular degeneration, or suppressing formation of drusen. Another object of the invention is to provide a pharmaceutical capable of treating and/or preventing age-related macular degeneration, particularly exudative age-related macular degeneration or atrophic age-related macular degeneration.

The present invention provides a compound of formula (I):

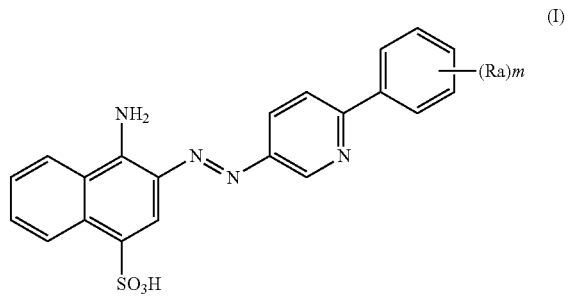

wherein
Ra is independently selected from the group consisting of halo, hydroxy, alkyl, halo-substituted alkyl, aryl, halo- or alkyl-substituted aryl, alkoxy, hydroxy- or carboxy-substituted alkoxy, aryloxy, halo- or alkyl-substituted aryloxy, CHO, C(O)-alkyl, C(O)-aryl, C(O)-alkyl-carboxyl, C(O)-alkylene-carboxy ester and cyano, and
m is an integer selected from 0 to 4,
or an oxide, ester, prodrug, pharmaceutically acceptable salt or solvate thereof for removing drusen, suppressing formation of drusen, and/or treating and/or preventing age-related macular degeneration (hereinafter referred to as the compound of the invention).

In a further aspect, the present invention provides a pharmaceutical composition for removing drusen, suppressing formation of drusen, and/or creating and/or preventing age-related macular degeneration comprising the compound of formula (I) or the oxide, ester, prodrug, pharmaceutically acceptable salt or solvate thereof.

In a further aspect, the present invention provides use of the compound of formula (I) or the oxide, ester, prodrug, pharmaceutically acceptable salt or solvate thereof for manufacturing a pharmaceutical composition for removing drusen, suppressing formation of drusen, and/or treating and/or preventing age-related macular degeneration.

In a further aspect, the present invention provides a method for removing drusen, suppressing formation of drusen, and/or treating and/or preventing age-related macular degeneration comprising administering a therapeutically effective amount of the compound of formula (I) or the oxide, ester, prodrug, pharmaceutically acceptable salt or solvate thereof to a subject in need thereof.

In a further aspect, age-related macular degeneration is exudative age-related macular degeneration or atrophic age-related macular degeneration, particularly atrophic age-related macular degeneration.

In a further aspect, the compound of formula (I) or the oxide, ester, prodrug, pharmaceutically acceptable salt or solvate thereof is administered orally.

The compound of the invention is capable of removing drusen, which are the precursor lesions of age-related macular degeneration, or suppressing the formation of the drusen. Therefore, the present invention provides an agent for treating and/or preventing age-related macular degeneration which works with a novel mechanism. Specially, the compound of the invention is useful for treating atrophic age-related macular degeneration, for which no effective therapy has been established.

DESCRIPTION OF EMBODIMENTS

Definition

Figure 1:
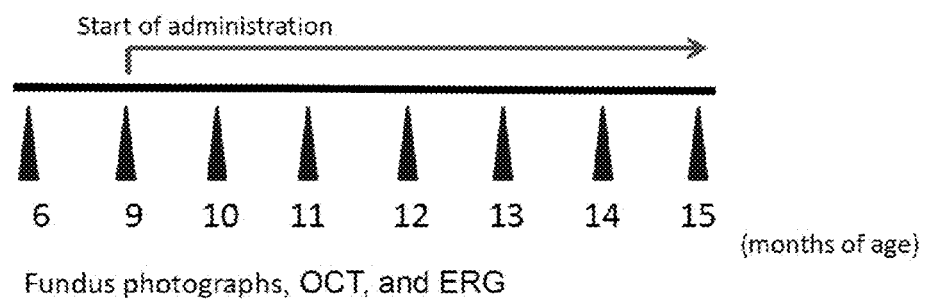
FIG. 1 shows scheme of Experiment 1.

Unless defined otherwise, the terms used herein have the meaning as commonly understood to those skilled in the an in the fields including organic chemistry, medicine, pharmacology, molecular biology, and microbiology. Definitions of several terms used herein are described below. The definitions herein take precedence over the general understanding.

"Alkyl" refers to a monovalent saturated aliphatic hydrocarbyl group having from 1 to 10 carbon atoms, preferably 1 to 6 carbon atoms. The term "$C_{x-y}$alkyl" refers to an alkyl group having from x to y carbon atoms. Examples of the alkyl include, but not limited to, linear and branched hydrocarbyl groups such as methyl($CH_3$—), ethyl($CH_3CH_2$—), n-propyl($CH_3CH_2CH_2$—), isopropyl(($CH_3)_2CH$—), n-butyl ($CH_3CH_2CH_2CH_2$—), isobutyl(($CH_3)_2CHCH_2$—), sec-butyl(($CH_3)(CH_3CH_2)CH$—), t-butyl(($CH_3)_3C$—), n-pentyl ($CH_3CH_2CH_2CH_2CH_2$—), and neopentyl(($CH_3)_3CCH_2$—).

"Substituted" as a word qualifying a name of a group means that one or more hydrogen atom of the group is, identically or differently, replaced by one or more substituent defined herein.

"Alkylene" refers to a divalent saturated aliphatic hydrocarbyl group having from 1 to 10 carbon atoms, preferably 1 to 6 carbon atoms. The term "$C_{x-y}$alkylene" refers to an alkylene group having from x to y carbon atoms. Alkylidene and alkylene groups include branched and straight chain hydrocarbyl groups.

"Alkoxy" refers to the group —O-alkyl in which alkyl is as defined herein. Examples of the alkoxy include methoxy, ethoxy, n-propoxy, isopropoxy, n-butoxy, t-butoxy, sec-butoxy, and n-pentoxy.

"Aryl" or "Ar" refers to a monovalent aromatic carbocyclic group of from 6 to 14 carbon atoms having a single ring (e.g., phenyl) or multiple condensed rings (e.g., naphthyl or anthryl). Typical aryl groups include phenyl and naphthyl.

"Aryloxy" refers to the group —O-aryl in which aryl is as defined herein. Examples of the aryloxy include phenoxy and naphthoxy.

"Cyano" or "carbonitrile" refers to the group —CN.

"Carboxyl" or "carboxy" refers to the group —COOH or a salt thereof.

"Carboxyl ester" or "carboxy ester" refers to the group —C(O)O-alkyl in which alkyl is as defined herein.

"Halo" or "halogen" refers to fluoro, chloro, bromo or iodo.

"Hydroxy" or "hydroxyl" refers to the group —OH.

Unless indicated otherwise, a substituent that is not explicitly defined herein is named by describing the name of the terminal functional group of the substituent first and sequentially describing the adjacent functional group toward the point binding to the rest of the compound. For example, the substituent "arylalkyloxycarbonyl" refers to (aryl)-(alkyl)-O—C(O)—.

It is understood that the definitions described above are not intended to include impermissible substitution patterns (e.g., methyl substituted with five fluoro groups). Those skilled in the art are familiar with such impermissible substitution patterns.

"Compound" as used herein refers to a compound encompassed by formula (I) disclosed herein and a specific compound represented by formula (I) including the oxides, esters, prodrugs, pharmaceutically acceptable salts, and solvates thereof. The term further includes the stereoisomers and tautomers of the compound or compounds.

"Solvate" of a compound refers to a compound, where the compound is as defined above, that is bound to a stoichiometric or non-stoichiometric amount of a solvent. Solvates includes solvates of an oxide, ester, prodrug, or pharmaceutically acceptable salt of the compound of formula (I). The solvent is volatile, non-toxic, and/or acceptable for administration to a human in a trace amount. Suitable solvates include water.

"Stereoisomer" refers to a compound that differs only in the chirality at one or more stereocenters from a compound having the same structure. Stereoisomers include enantiomers and diastereomers.

"Tautomer" refers to an alternate form of a compound that has a proton at a different position, such as enol-keto and imine-enamine tautomers. It also refers to a tautomeric form of a heteroaryl group containing a ring atom attached to both a ring —NH— moiety and a ring =N— moiety, such as pyrazoles, imidazoles, benzimidazoles, triazoles, and tetrazoles.

"Pharmaceutically acceptable salt" refers to a pharmaceutically acceptable salt derived from any of a variety of organic and inorganic counter ions well known in the art and includes, for example, salts of sodium, potassium, calcium, magnesium, ammonium, and tetraalkylammonium, and salts of organic or inorganic acids, such as hydrochloride, hydrobromide, tartrate, mesylate, acetate, maleate, and oxalate. Pharmaceutically acceptable salts include oxides, esters, or prodrugs of the compounds of formula (I).

As used herein, the term "pharmaceutically acceptable salt" includes nontoxic acid or alkaline earth metal salts of the compounds of formula (I). These salts can be prepared in situ during the final isolation and purification of the compounds of formula (I), or by separately reacting the base or acid functions in the compounds with a suitable organic or inorganic acid or base, respectively. Representative salts include, but are not limited to, acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. The basic nitrogen-containing groups may be quaternized with reactive agents including alkyl halides, such as methyl, ethyl, propyl, and butyl chloride, bromides, and iodides; dialkyl sulfates, such as dimethyl, diethyl, dibutyl, and diamyl sulfates; long chain halides, such as decyl, lauryl, myristyl and stearyl chlorides, bromides and iodides; aralkyl halides such as benzyl and phenethyl chlorides. Water or oil-soluble or dispersible products are thereby obtained.

Examples of the acid which may be employed to form pharmaceutically acceptable acid addition salts include inorganic acids such as hydrochloric acid, sulfuric acid and phosphoric acid, and organic acids such as oxalic acid, maleic acid, methanesulfonic acid, succinic acid and citric acid. Base addition salts can be prepared in situ during the final isolation and purification of the compounds of formula (I), or by separately reacting the carboxylic acid groups of the compounds with a suitable base such as hydroxide, carbonate or bicarbonate of a pharmaceutically acceptable metal cation, or ammonia, or an organic primary, secondary or tertiary amine. Pharmaceutically acceptable salts include, but are not limited to, cations of the alkali and alkaline earth metals, such as sodium, lithium, potassium, calcium, magnesium, and aluminum salts, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine. Other representative organic amines useful for the formation of base addition salts include diethylamine, ethylenediamine, ethanolamine, diethanolamine, and piperazine.

The term "pharmaceutically acceptable ester" as used herein, refers to an ester that hydrolyzes in vivo and includes those that break down readily in a human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than six carbon atoms. Examples of particular esters include formates, acetates, propionates, butyrates, acrylates and ethylsuccinates.

The term "pharmaceutically acceptable prodrug" as used herein refers to a prodrug of the compound which is, within the scope of sound medical judgment, suitable for use in contact with the tissues of humans and animals without an undue adverse effect such as toxicity, irritation, and allergic response, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the formula above, for example by hydrolysis in blood. A general discussion, is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

It will be apparent to those skilled in the art that the compounds of formula (I) or the pharmaceutically acceptable salts, esters, oxides, and prodrugs of any of them, may be processed in vivo through metabolism in a human or animal body or cell to produce metabolites. The term "metabolite" as used herein refers to any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives. The metabolites of a compound of the invention may be identified using routine techniques known in the art. See, e.g., Bertolini, G. et al., J. Med. Chem. 40:2011-2016 (1997); Shan, D. et al., J. Pharm. Sci. 86(7):

765-767; Bagshawe K., Drug Dev. Res. 34:220-230 (1995); Bodor, N., Advances in Drug Res. 13:224-331 (1984); Bundgaard, H., Design of Prodrugs (Elsevier Press 1985); and Larsen, I. K., Design and Application, of Prodrugs, Drug Design and Development (Krogsgaard-Larsen. et al., eds., Harwood Academic Publishers, 1991). It should be understood that individual chemical compounds that are metabolites of the compounds of formula (I) or the pharmaceutically acceptable salts, esters, oxides and prodrugs of any of them, are included within the embodiments provided herein.

The term "subject" refers to a mammal and includes humans and non-human, mammals.

The term "preventing" or "prevention" of a disease in a subject refers to preventing the disease from occurring in a subject that is predisposed or does not yet display symptoms of the disease. The term "creating" or "treatment" of a disease in a subject, refers to 1) inhibiting the disease or arresting its development; or 2) ameliorating or causing regression of the disease.

In an embodiment, the compound of the invention is the compound of formula (I) wherein Ra is independently selected from the group consisting of halo, hydroxy, alkyl, halo-substituted alkyl and alkoxy, or an oxide, ester, prodrug, pharmaceutically acceptable salt or solvate thereof.

In an embodiment, the compound of the invention is the compound of formula (I) wherein Ra is independently selected from the group consisting of halo and alkyl, or an oxide, ester, prodrug, pharmaceutically acceptable salt or solvate thereof.

In an embodiment, the compound of the invention is the compound of formula (I) wherein the compound has two Ra groups, one of the Ra group is halo and the other is alkyl, or an oxide, ester, prodrug, pharmaceutically acceptable salt or solvate thereof.

In an embodiment, the compound of the invention is the compound selected from Compounds 1 to 53 listed in Table 1 below, or an oxide, ester, prodrug, pharmaceutically acceptable salt or solvate thereof.

TABLE 1

| No. | Structure | Compound Name |
|---|---|---|
| 1 | 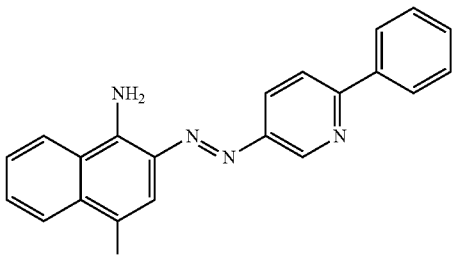 | 4-amino-3-(6-phenylpyridine-3-ylazo)naphthalene-1-sulfonic acid sodium salt |
| 2 | 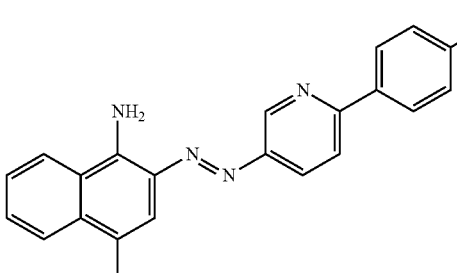 | 4-amino-3-(6-p-tolylpyridine-3-ylazo)naphthalene-1-sulfonic acid sodium salt |
| 3 | 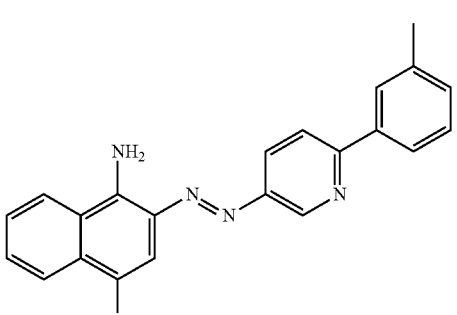 | 4-amino-3-(6-m-tolylpyridine-3-ylazo)naphthalene-1-sulfonic acid sodium salt |

TABLE 1-continued

| No. | Structure | Compound Name |
|---|---|---|
| 4 | 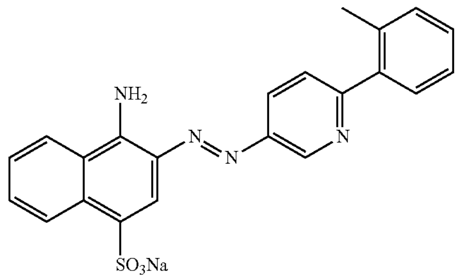 | 4-amino-3-(6-o-tolylpyridine-3-ylazo)naphthalene-1-sulfonic acid sodium salt |
| 5 | 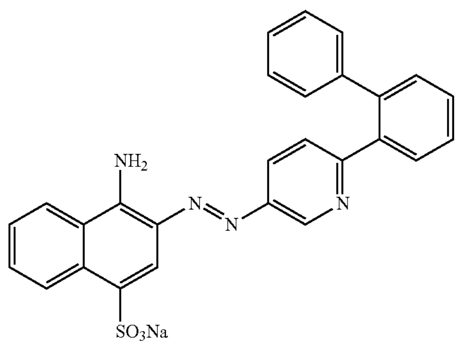 | 4-amino-3-(6-biphenyl-2-ylpyridine-3-ylazo)naphthalene-1-sulfonic acid sodium salt |
| 6 | 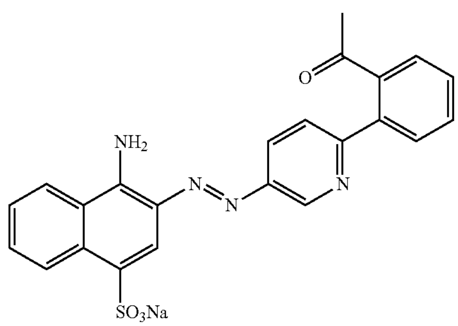 | 3-[6-(2-acetylphenyl)pyridine-3-ylazo]-4-aminonaphthalene-1-sulfonic acid sodium salt |
| 7 | 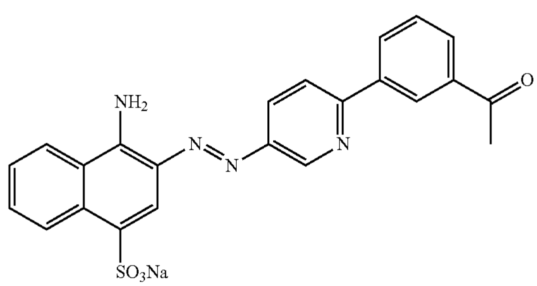 | 3-[6-(3-acetylphenyl)pyridine-3-ylazo]-4-aminonaphthalene-1-sulfonic acid sodium salt |
| 8 | 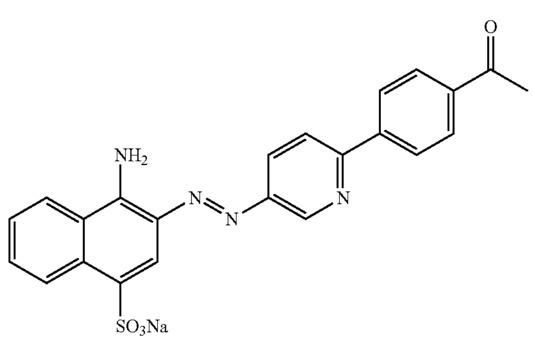 | 3-[6-(4-acetylphenyl)pyridine-3-ylazo]-4-aminonaphthalenesulfonic acid sodium salt |

TABLE 1-continued

| No. | Structure | Compound Name |
|---|---|---|
| 9 | 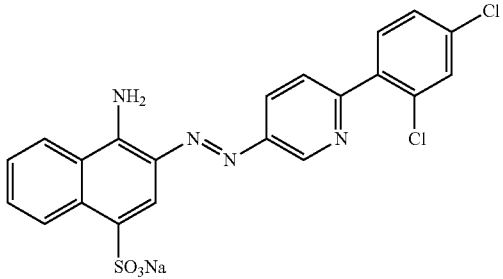 | 4-amino-3-[6-(2,4-dichlorophenyl)pyridine-3-ylazo]naphthalene-1-sulfonic acid sodium salt |
| 10 | 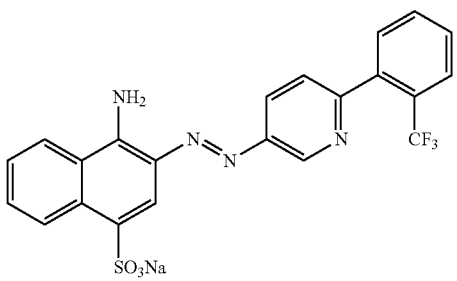 | 4-amino-3-[6-(2-trifluoromethylphenyl)pyridine-3-ylazo]naphthalene-1-sulfonic acid sodium salt |
| 11 | 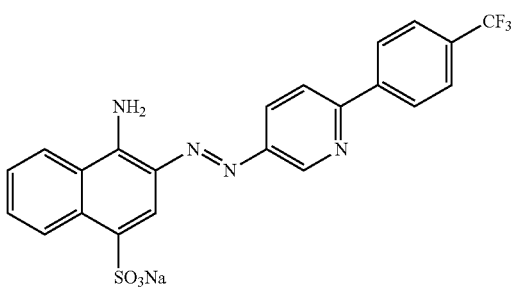 | 4-amino-3-[6-(4-trifluoromethylphenyl)pyridine-3-ylazo]naphthalene-1-sulfonic acid sodium salt |
| 12 | 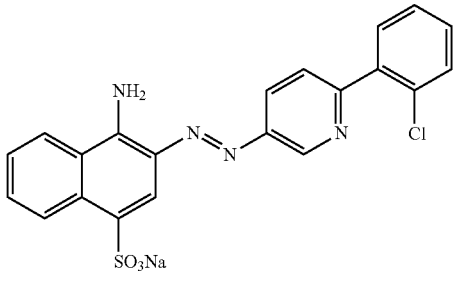 | 4-amino-3-[6-(2-chlorophenyl)pyridine-3-ylazo]naphthalene-1-sulfonic acid sodium salt |
| 13 | 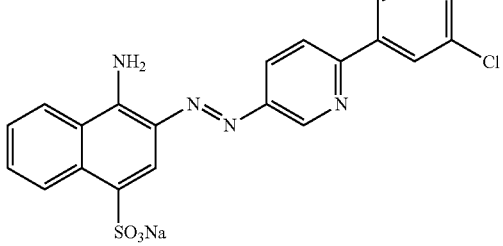 | 4-amino-3-[6-(3-chlorophenyl)pyridine-3-ylazo]naphthalene-1-sulfonic acid sodium salt |

TABLE 1-continued

| No. | Structure | Compound Name |
|---|---|---|
| 14 | 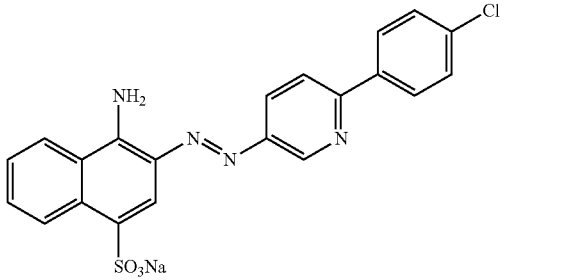 | 4-amino-3-[6-(4-chlorophenyl)pyridine-3-ylazo]naphthalene-1-sulfonic acid sodium salt |
| 15 | 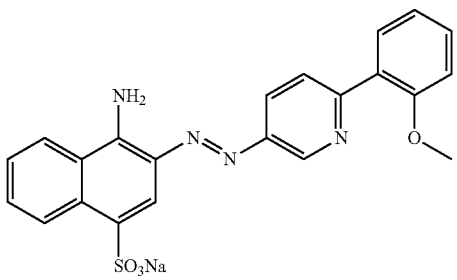 | 4-amino-3-[6-(2-methoxyphenyl)pyridine-3-ylazo]naphthalene-1-sulfonic acid sodium salt |
| 16 | 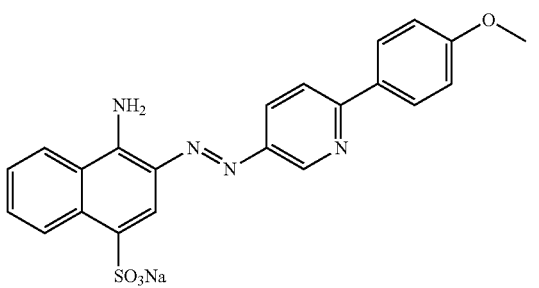 | 4-amino-3-[6-(4-methoxyphenyl)pyridine-3-ylazo]naphthalene-1-sulfonic acid sodium salt |
| 17 | 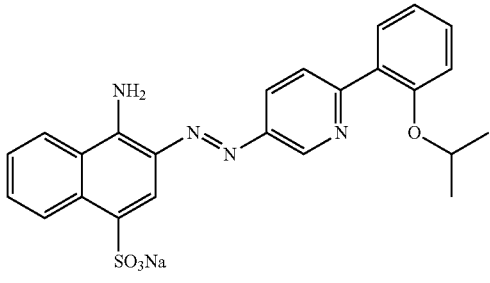 | 4-amino-3-[6-(2-isopropoxyphenyl)pyridine-3-ylazo]naphthalene-1-sulfonic acid sodium salt |
| 18 | 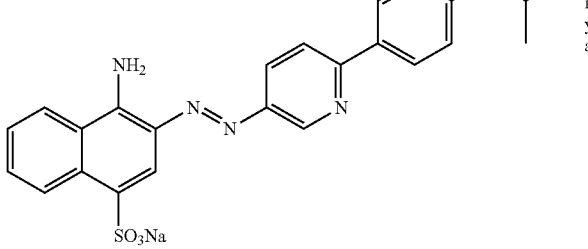 | 4-amino-3-[6-(4-isopropoxyphenyl)pyridine-3-ylazo]naphthalene-1-sulfonic acid sodium salt |

TABLE 1-continued

| No. | Structure | Compound Name |
|---|---|---|
| 19 | 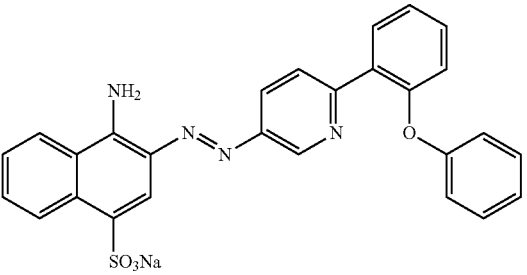 | 4-amino-3-[6-(2-phenoxyphenyl)pyridine-3-ylazo]naphthalene-1-sulfonic acid sodium salt |
| 20 | 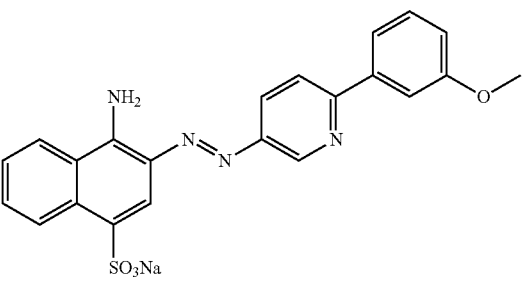 | 4-amino-3-[6-(3-methoxyphenyl)pyridine-3-ylazo]naphthalene-1-sulfonic acid sodium salt |
| 21 | 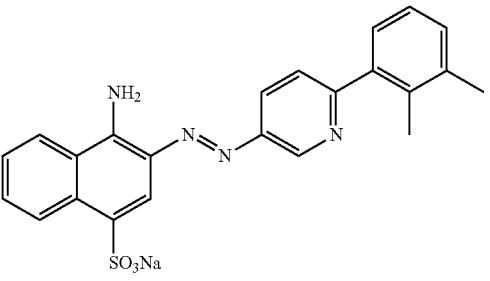 | 4-amino-3-[6-(2,3-dimethylphenyl)pyridine-3-ylazo]naphthalene-1-sulfonic acid sodium salt |
| 22 | 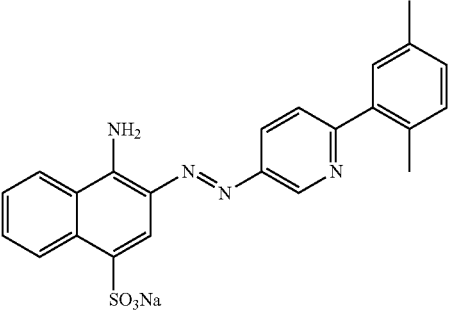 | 4-amino-3-[6-(2,5-dimethylphenyl)pyridine-3-ylazo]naphthalene-1-sulfonic acid sodium salt |
| 23 | 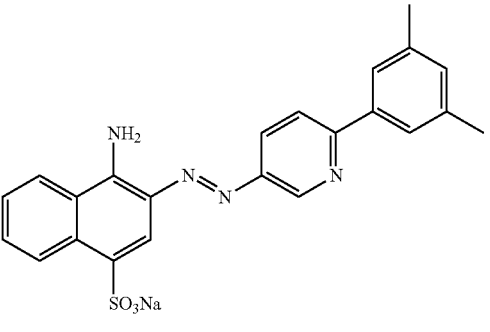 | 4-amino-3-[6-(3,5-dimethylphenyl)pyridine-3-ylazo]naphthalene-1-sulfonic acid sodium salt |

TABLE 1-continued

| No. | Structure | Compound Name |
|---|---|---|
| 24 | 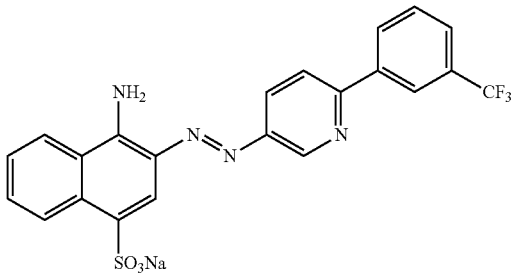 | 4-amino-3-[6-(3-trifluoromethylphenyl)pyridine-3-ylazo]naphthalene-1-sulfonic acid sodium salt |
| 25 | 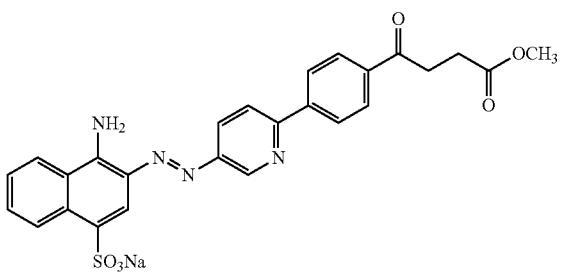 | methyl 4-{4-[5-(1-amino-4-sulfonaphthalene-2-ylazo)pyridine-2-yl]phenyl}-4-oxobutyrate sodium salt |
| 26 | 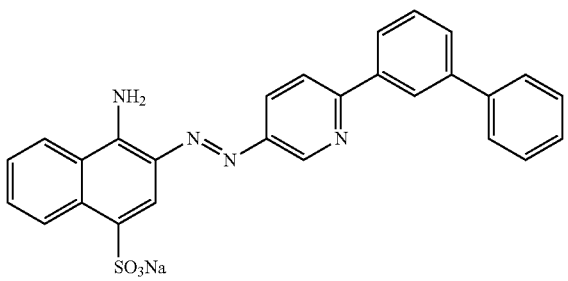 | 4-amino-3-(6-biphenyl-3-ylpyridine-3-ylazo)naphthalene-1-sulfonic acid sodium salt |
| 27 | 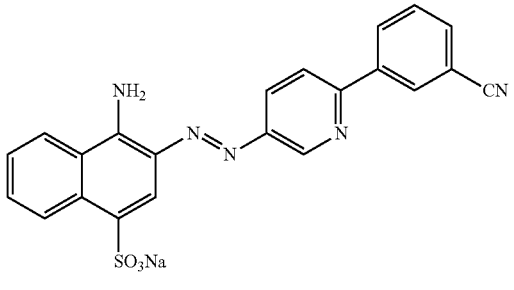 | 4-amino-3-[6-(3-cyanophenyl)pyridine-3-ylazo]naphthalene-1-sulfonic acid sodium salt |
| 28 | 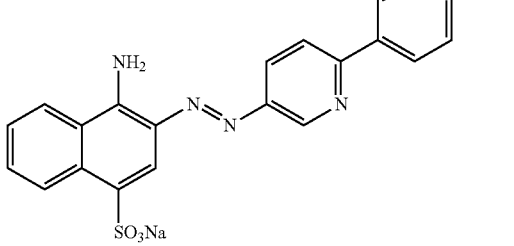 | 4-amino-3-[6-(4-cyanophenyl)pyridine-3-ylazo]naphthalene-1-sulfonic acid sodium salt |

TABLE 1-continued

| No. | Structure | Compound Name |
|---|---|---|
| 29 | 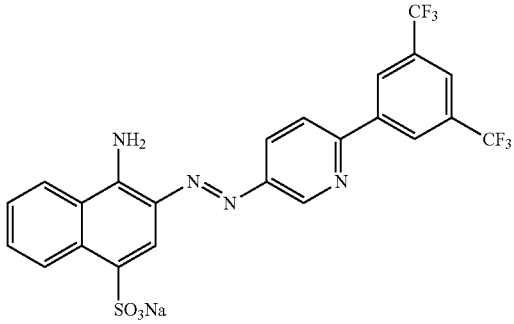 | 4-amino-3-[6-(3,5-bistrifluoromethylphenyl)pyridine-3-ylazo]naphthalenesulfonic acid sodium salt |
| 30 | 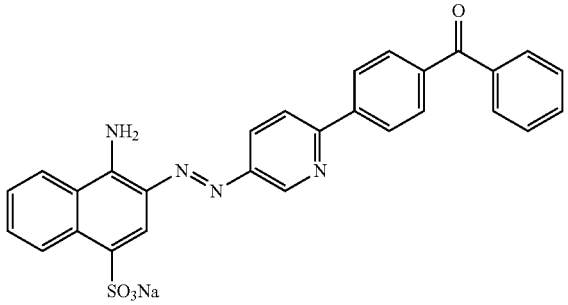 | 4-amino-3-[6-(4-benzoylphenyl)pyridine-3-ylazo]naphthalene-1-sulfonic acid sodium salt |
| 31 | 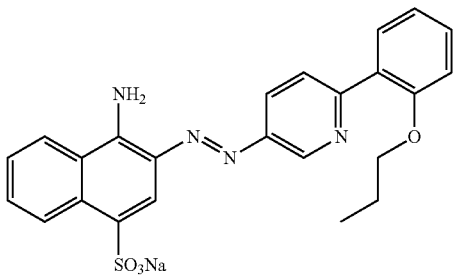 | 4-amino-3-[6-(2-propoxyphenyl)pyridine-3-ylazo]naphthalene-1-sulfonic acid sodium salt |
| 32 | 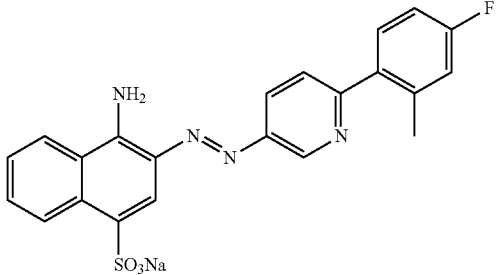 | 4-amino-3-[6-(4-fluoro-2-methylphenyl)pyridine-3-ylazo]naphthalene-1-sulfonic acid sodium salt |
| 33 | 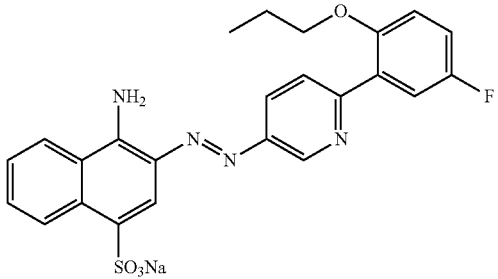 | 4-amino-3-[6-(5-fluoro-2-propoxyphenyl)pyridine-3-ylazo]naphthalene-1-sulfonic acid sodium salt |

TABLE 1-continued

| No. | Structure | Compound Name |
|---|---|---|
| 34 | 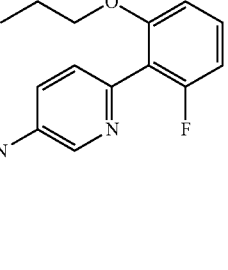 | 4-amino-3-[6-(2-fluoro-6-propoxyphenyl)pyridine-3-ylazo]naphthalene-1-sulfonic acid sodium salt |
| 35 | 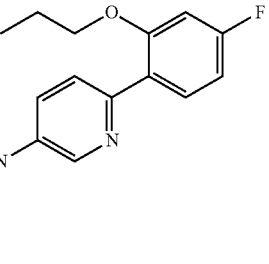 | 4-amino-3-[6-(4-fluoro-2-propoxyphenyl)pyridine-3-ylazo]naphthalene-1-sulfonic acid sodium salt |
| 36 | 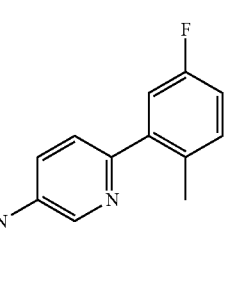 | 4-amino-3-[6-(5-fluoro-2-methylphenyl)pyridine-3-ylazo]naphthalene-1-sulfonic acid sodium salt |
| 37 | 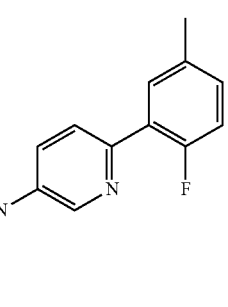 | 4-amino-3-[6-(2-fluoro-5-methylphenyl)pyridine-3-ylazo]naphthalene-1-sulfonic acid sodium salt |
| 38 | 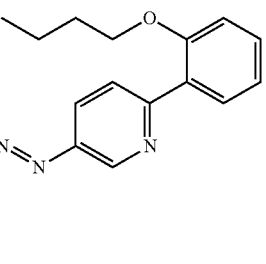 | 4-amino-3-[6-(2-butoxyphenyl)pyridine-3-ylazo]naphthalene-1-sulfonic acid sodium salt |

TABLE 1-continued

| No. | Structure | Compound Name |
|---|---|---|
| 39 | 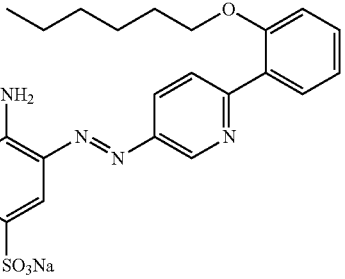 | 4-amino-3-[6-(2-hexyloxyphenyl)pyridine-3-ylazo]naphthalene-1-sulfonic acid sodium salt |
| 40 | 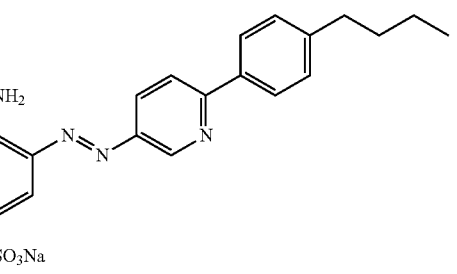 | 4-amino-3-[6-(4-butylphenyl)pyridine-3-ylazo]naphthalene-1-sulfonic acid sodium salt |
| 41 | 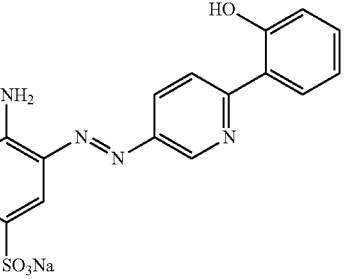 | 4-amino-3-[6-(2-hydroxyphenyl)pyridine-3-ylazo]naphthalene-1-sulfonic acid sodium salt |
| 42 | 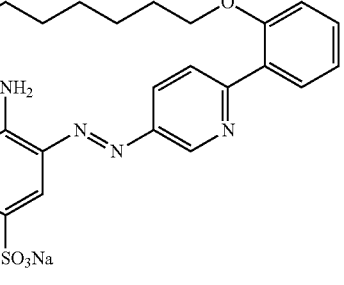 | 4-amino-3-{6-[2-(6-hydroxyhexyloxy)phenyl]pyridine-3-ylazo)naphthalene-1-sulfonic acid sodium salt |
| 43 | 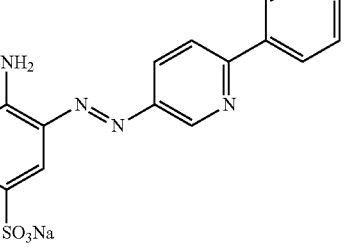 | 4-{2-[5-(1-amino-4-sulfonaphthalene-2-ylazo)pyridine-2-yl]phenoxy}butyric acid disodium salt |

TABLE 1-continued

| No. | Structure | Compound Name |
|---|---|---|
| 44 | 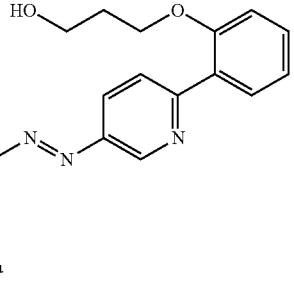 | 4-amino-3-{6-[2-(3-hydroxypropoxy)phenyl]pyridine-3-ylazo}naphthalene-1-sulfonic acid sodium salt |
| 45 | 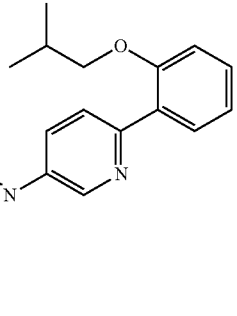 | 4-amino-3-[6-(2-isobutoxyphenyl)pyridine-3-ylazo]naphthalene-1-sulfonic acid sodium salt |
| 46 | 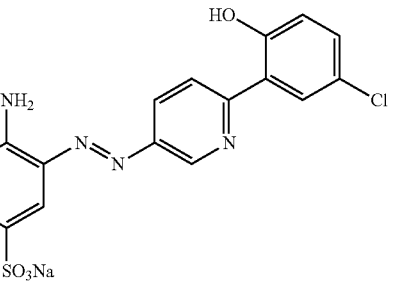 | 4-amino-3-[6-(5-chloro-2-hydroxyphenyl)pyridine-3-ylazo]naphthalene-1-sulfonic acid sodium salt |
| 47 | 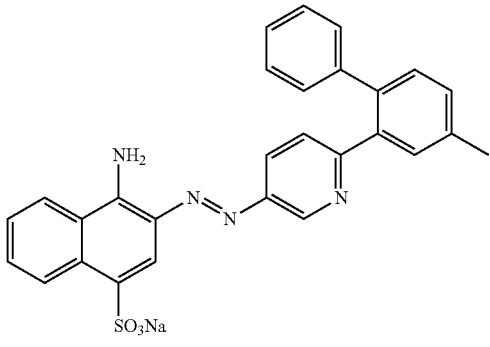 | 4-amino-3-[6-(4-methylbiphenyl-2-yl)pyridine-3-ylazo]naphthalene-1-sulfonic acid sodium salt |
| 48 | 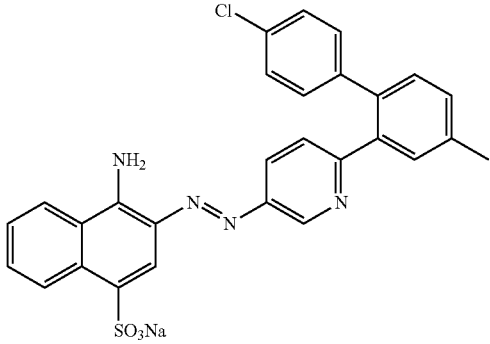 | 4-amino-3-[6-(4'-chloro-4-methylbiphenyl-2-yl)pyridine-3-ylazo]naphthalene-1-sulfonic acid sodium salt |

TABLE 1-continued

| No. | Structure | Compound Name |
|---|---|---|
| 49 | 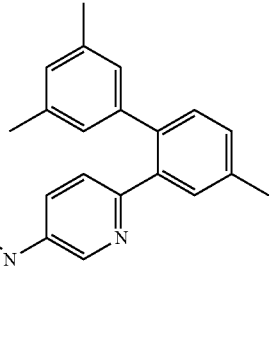 | 4-amino-3-[6-(4,3',5'-trimethylbiphenyl-2-yl)pyridine-3-ylazo]naphthalene-1-sulfonic acid sodium salt |
| 50 | 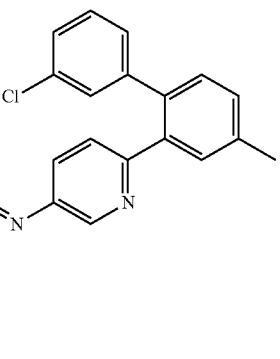 | 4-amino-3-[6-(3'-chloro-4-methylbiphenyl-2-yl)pyridine-3-ylazo]naphthalene-1-sulfonic acid sodium salt |
| 51 | 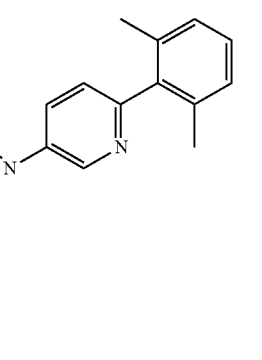 | 4-amino-3-[6-(2,6-dimethylphenyl)pyridine-3-ylazo]naphthalene-1-sulfonic acid sodium salt |
| 52 | 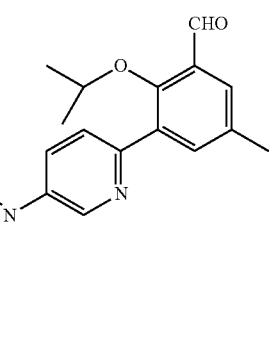 | 4-amino-3-[6-(3-formyl-2-isopropoxy-5-methylphenyl)pyridine-3-ylazo]naphthalene-1-sulfonic acid sodium salt |

TABLE 1-continued

| No. | Structure | Compound Name |
|---|---|---|
| 53 | 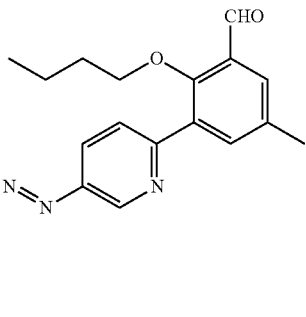 | 4-amino-3-[6-(3-formyl-2-butoxy-5-methylphenyl)pyridine-3-ylazo]naphthalene-1-sulfonic acid sodium salt |

In an embodiment, the compound of the invention is the compound of the formula

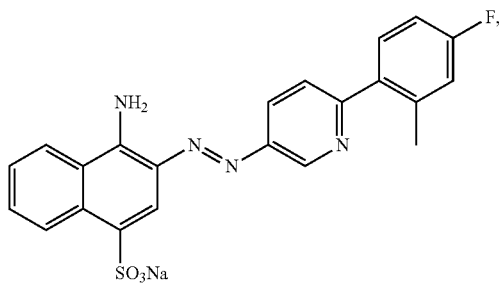

which is Compound 32 listed in the table above, or an oxide, ester, prodrug, pharmaceutically acceptable salt or solvate thereof, particularly a sodium salt thereof.

It will also be apparent to those skilled in the art that the compound of formula (I), or the pharmaceutically acceptable salt, ester, oxide, and prodrug thereof may be subject to tautomerization and may exist in various tautomeric forms.

The compound of formula (I) as well as the pharmaceutically acceptable salt, ester, oxide, and prodrug thereof may comprise an asymmetrically substituted carbon atom. Such asymmetrically substituted carbon atom may result in the compound existing in enantiomers, diastereomers, and other stereoisomeric forms that may be defined, in terms of absolute stereochemistry, such as in (R)- or (S)-forms. As a result, all such possible isomers, individual stereoisomers in their optically pure forms, mixtures thereof, racemic mixtures (or "racemates"), mixtures of diastereomers, as well as single diastereomers of the compounds are contemplated. The terms "S" and "R" configurations, as used herein, are as defined by the IUPAC 1974 RECOMMENDATIONS FOR SECTION E, FUNDAMENTAL STEREOCHEMISTRY, Pure Appl. Chem. 45:13-30 (1976).

The method for synthesizing the compounds of formula (I), especially the compounds of numbers 1 to 53, is described in WO2012/014394 and WO2012/043891 in detail, the contents of which are incorporated herein by reference in their entirety.

Age-Related Macular Degeneration

Age-related macular degeneration is divided to two types: exudative (wet) or atrophic (dry). Essential features of exudative age-related macular degeneration are choroidal neovascularization (CNV) and its proliferative change caused by deterioration of layers of retinal pigment epithelial cells, Bruch's membrane and choroid in the macular area. The CNV develops under retinal pigment epithelium and then under retina. Hemorrhage and effusion from the CNV cause detachment of retinal pigment epithelium and retinal detachment. After absorbance of the blood or effusion, an atrophy or scar is formed, causing permanent severe reduced vision. Exudative age-related macular degeneration proceeds rapidly. In the case of atrophic age-related macular degeneration, geographic atrophy lesions are formed in retinal pigment epithelium and choriocapillaris in the macular area. Atrophic age-related macular degeneration proceeds slowly.

Retinal pigment epithelial cells play an important role in retaining environment of neural retina for example by phagocytosing photoreceptor outer segments. In association with aging, lipofuscin accumulates in the cells as digestion residues, fatty degeneration of the cells occurs, and then abnormal structures called drusen are formed. In addition, Bruch's membrane under pigment epithelium becomes thick in association with aging. As a result, physiological environment between a layer of visual cells, a layer of retinal pigment epithelium, and Bruch's membrane is changed. Chronic inflammation or ischemia caused by such change is thought to induce the neovascularization from choroid. Vascular endothelial growth factor (VEGF) is one of the physiologically active substances which exerts the greatest effect on the development and growth of the neovessels. The CNV develops from the damaged part of the Bruch's membrane to retinal pigment epithelium and subretina.

No effective therapy is currently available for atrophic age-related macular degeneration. Effective therapy for exudative age-related macular degeneration is vascular regression therapy (intravitreal administration of anti-VEGF agents or photodynamic therapy) for established neovessels only. The compounds of formula (I) of the present invention may prevent the drusen from developing into exudative or atrophic age-related macular degeneration by a mechanism different from that of the vascular regression therapy, namely by removing the drusen or suppressing the formation of the drusen.

Though the compound of formula (I) of the present invention is capable of treating exudative or atrophic age-related macular degeneration with the mechanism different from that of the vascular regression therapy, this does not imply excluding the combination of the therapy with the compound of the present invention and the vascular regression therapy. Examples of the vascular regression therapy that may be used in combination with the compound of the present invention include, but are not limited to, intravitreal administration of ranibizumab, pegaptanib or aflibercept as well as photodynamic therapy.

Administration and Pharmaceutical Composition

An embodiment of the present invention provides a pharmaceutical composition for removing drusen, suppressing formation of drusen, and/or treating and/or preventing age-related macular degeneration comprising at least one compound of formula (I), either alone or together with a further agent, together with a pharmaceutically acceptable carrier suitable for administration to a human or animal subject.

An embodiment of the present invention provides the compound of formula (I) for removing drusen, suppressing formation of drusen, and/or treating and/or preventing age-related macular degeneration. A further embodiment of the present invention provides use of the compound of formula (I) for manufacturing a pharmaceutical composition for removing drusen, suppressing formation of drusen, and/or treating and/or preventing age-related macular degeneration.

In general, the compound of the invention is administered in a therapeutically effective amount by any of the accepted modes of administration for agents that serve similar utilities. The actual amount of the compound, i.e., the active ingredient, depends upon numerous factors such as the severity of the disease to be treated, the age and relative health of the subject, the potency of the used compound, the route and form of administration, and other factors. The compound of the invention may be administered more than once a day, preferably three or four times a day. All of these factors are within the skill of the attending clinician.

The amount of the active ingredient that may be combined with a carrier material to produce a single dosage form will vary depending upon the host to be treated and the particular mode of administration. It will be understood, however, that the specific dose level for any particular subject will depend upon a variety of factors including the activity of the specific compound employed, the age, body weight, general health, sex, and diet of the subject, the time and route of the administration, the rate of the excretion, the drug combination, and the severity of the specific disease to be treated. The therapeutically effective amount for a given situation can be readily determined by routine experimentation and is within the skill and judgment of the ordinary clinician.

A therapeutically effective amount generally can be a total daily dose administered to a host in single or divided doses which may be in amounts, for example, of from about 0.001 to about 1000 mg/kg body weight daily and from about 1.0 to about 30 mg/kg body weight daily. A dosage unit composition may contain such amounts of submultiples thereof to make up the daily dose.

Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, and ion exchange resins, as well as combinations of any two or more thereof. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil. In some embodiments, liquid carriers, particularly for injectable solutions, include water, saline, aqueous dextrose, and glycols. Other suitable pharmaceutically acceptable excipients are described in "Remington's Pharmaceutical Sciences," Mack Pub. Co., New Jersey (1991).

The choice of formulation depends on various factors such as the mode of drug administration and bioavailability of the drug substance. The drug can be administered as pharmaceutical compositions by any one of the following routes or combination of two or more of them: oral, systemic (e.g., transdermal, intranasal or by suppository), topical (ophthalmic, intravitreal, subconjunctival, Tenon capsule or transdermal administration) or parenteral administration, preferably oral, ophthalmic, intravitreal, subconjunctival or Tenon capsule administration. An exemplary manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another manner for administration is inhalation such as for delivering a therapeutic agent directly to the respiratory tract (see U.S. Pat. No. 5,607,915). Topical administration may also involve the use of transdermal administration such as transdermal patches or ionophoresis devices. The term "parenteral" as used herein includes subcutaneous injections, intravenous, intraperitoneal, intramuscular, intrasternal injection, or infusion techniques.

Injectable preparations, for example, sterile injectable aqueous or oleaginous suspensions may be formulated according to the known art using suitable dispersing or wetting agents or suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose fixed oils of any grade may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compound of the invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain agents such as stabilizers, preservatives, and excipients. Examples of lipids are the phospholipids and phosphatidyl cholines (lecithins), both natural and synthetic. Methods to form liposomes are known in the art. See, for example, Prescott, Ed., Methods in Cell Biology, Volume XIV, Academic Press, New York, N. W., p. 33 et seq. (1976).

Compressed gases may be used to disperse the compound of the invention in aerosol form. Inert gases suitable for this purpose include nitrogen and carbon dioxide. Other suitable pharmaceutical excipients and their formulations are described in Remington's Pharmaceutical Sciences, edited by E. W. Martin (Mack Publishing Company, 18th ed., 1990).

For delivery via inhalation the compound of the invention can be formulated as liquid solutions, suspensions, aerosol propellants or dry powder and loaded into a suitable dispenser for administration. There are several types of pharmaceutical inhalation devices, nebulizers, inhalers, metered dose inhalers (MDI) and dry powder inhalers (DPI). Nebulizer devices produce a stream of high velocity air that causes the therapeutic agents (which are formulated in a liquid form) to spray as a mist that is carried into the subject's respiratory tract. MDIs typically are formulation packaged with a compressed gas. Upon actuation, the device discharges a measured amount of therapeutic agent by the compressed gas, thus affording a reliable method of administering a set amount of the agent. DPI dispenses therapeutic agents in the form of a free flowing powder that can be dispersed in the subject's inspiratory air-stream during breaching by the device. In order to achieve a free flowing powder, the therapeutic agent is formulated with an excipient such as lactose. A measured amount of the therapeutic agent is stored in a capsule form and is dispensed with each actuation.

The compound of the invention may be administered in the form of an eye drop. The eye drop may be prepared by selecting and using as necessary, an isotonizing agent such as sodium chloride or concentrated glycerin; a buffer such as sodium phosphate or sodium, acetate; a surfactant such as polyoxyethylene sorbitan monooleate, polyoxyl stearate 40, or polyoxyethylene hardened castor oil; a stabilizer such as sodium citrate or sodium edetate; and a preservative such as benzalkonium chloride or paraben, and pH may be within a range accepted for ophthalmic formulation, and usually within a range of 4 to 8. An eye ointment may be prepared by using a generally used base such as white petrolatum or liquid paraffin.

EXAMPLES

The following Examples illustrate the present invention, but not limit the scope thereof.

Example 1

Compound 32: Synthesis of 4-amino-3-[6-(4-fluoro-2-methylphenyl)pyridine-3-ylazo]naphthalene-1-sulfonic acid sodium salt

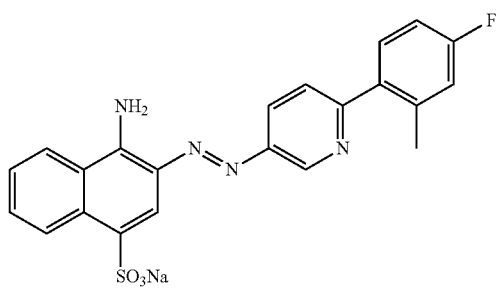

(i) 2-(4-Fluoro-2-methylphenyl)-5-nitropyridine

2-Chloro-5-nitropyridine (5.0 g, 31.5 mmol) and tetrakis (triphenylphosphine)palladium (0.35 g, 0.3 mmol) were added to 1,2-dimethoxyethan (50 ml), then degassed and purged with nitrogen three times under reduced pressure. Under nitrogen atmosphere the mixture was stirred at room temperature for 20 minutes, 4-fluoro-2-methylphenylboronic acid (31.5 mmol) and 2M aqueous sodium carbonate (31.5 ml) were poured in, and the temperature was raised to 80° C. After the reaction an 80° C. for 3 hours, the mixture was cooled to room temperature and extracted with addition of ethyl acetate and water. The organic layer was dried with anhydrous sodium sulfate, and concentrated under reduced pressure. The products were purified by column chromatography to give the title compound.

(ii) 6-(4-Fluoro-2-methylphenyl)pyridine-3-ylamine

Ethanol (20 ml) and water (5 ml) was mixed, added with iron powder, and heated to 70-80° C. Ammonium chloride (0.1 g, 2.1 mmol) was added, followed by 2-(4-fluoro-2-methylphenyl)-5-nitropyridine (2.0 g, 10.0 mmol) obtained in (i). The reaction was carried out at 70-80° C. for 1 hour. After the completion of the reaction, the iron powder was filtered while hot through Celite, and the filtrate was concentrated under reduced pressure. The residue was dissolved in isopropyl alcohol, crystallized and filtered with addition of water to give the title compound.

(iii) 4-Amino-3-[6-(4-fluoro-2-methylphenyl)pyridine-3-ylazo]naphthalene-1-sulfonic acid sodium salt 6-(4-Fluoro-2-methylphenyl)pyridine-3-ylamine (58.9 mmol) obtained in (ii) was dissolved in 99% acetic acid (50 ml), and added with 35% hydrochloric acid (25 g) to form hydrochloride. With cooling on ice a 36% aqueous solution of sodium nitrite (12 g, 62.5 mmol) was added dropwise at 0-5° C., and the reaction was carried out for about 15 minutes. Amide sulfuric acid was added and the reaction was carried out for additional 5 minutes, resulting in a diazo solution. 4-Amino-1-naphthalenesulfonic acid (13.0 g, 58.4 mmol) was suspended in water (130 ml), and the pH of the suspension, was adjusted to pH 8 to 9 with 10% aqueous sodium hydroxide. The mixture was cooled to 5-10° C., and added dropwise with the obtained diazo solution at 5-10° C., during which 10% aqueous sodium hydroxide was added dropwise to keep the pH at 7 to 9. After the completion of the addition, the reaction was carried out at 5-10° C. for 1 hour, then the temperature was raised to room temperature. Salting-out was performed with saturated aqueous sodium chloride, and the precipitated crystals were filtered with suction. Purification by column chromatography gave the title compound.

$^1$H-NMR δ[ppm]=9.22 (1H, d, J=2.4 Hz), 8.76 (1H, d, J=8.1), 8.49-8.44 (2H, m), 8.34 (1H, s), 7.82 (2H, bs), 7.67-7.47 (4H, m), 7.21-7.11 (2H, m), 2.41 (3H, s)

$^{13}$C-NMR (DMSO-d6) δ[ppm]=163.5, 160.3, 158.2, 147.1, 146.7, 145.4, 138.8, 138.7, 136.1, 136.1, 132.4, 132.1, 131.8, 131.7, 129.2, 128.6, 128.3, 127.2, 125.1, 124.6, 124.2, 124.0, 117.3, 117.1, 116.6, 112.9, 112.6, 20.4, 20.4

Example 2

Experiment 1: Removal of Drusen in Aged Mice

The effect of the compound of number 32 (Compound 32) to remove previously formed drusen in relatively aged mice was tested. CCR2 (monocyte chemoattractant protein 1 (MCP-1) receptor) deficient mice were used. The mice in the group of Compound 32 (n=30 eyes) were orally administered with 50 mg/kg/day of Compound 32 dissolved in saline five days week from the age of nine months. The mice in the control group (n=48 eyes) were orally administered with the saline. The mice in the both groups were allowed to freely drink water. At the age of 6, 9, 10, 11, 12, 13, 14, and 15 months, the mice were examined by fundus photographs, optical coherence tomography (OCT) (Multiline OCT, Heidelberg Engineering) and electroretinogram (ERG). FIG. 1 shows the scheme of Experiment 1.

Figure 2:
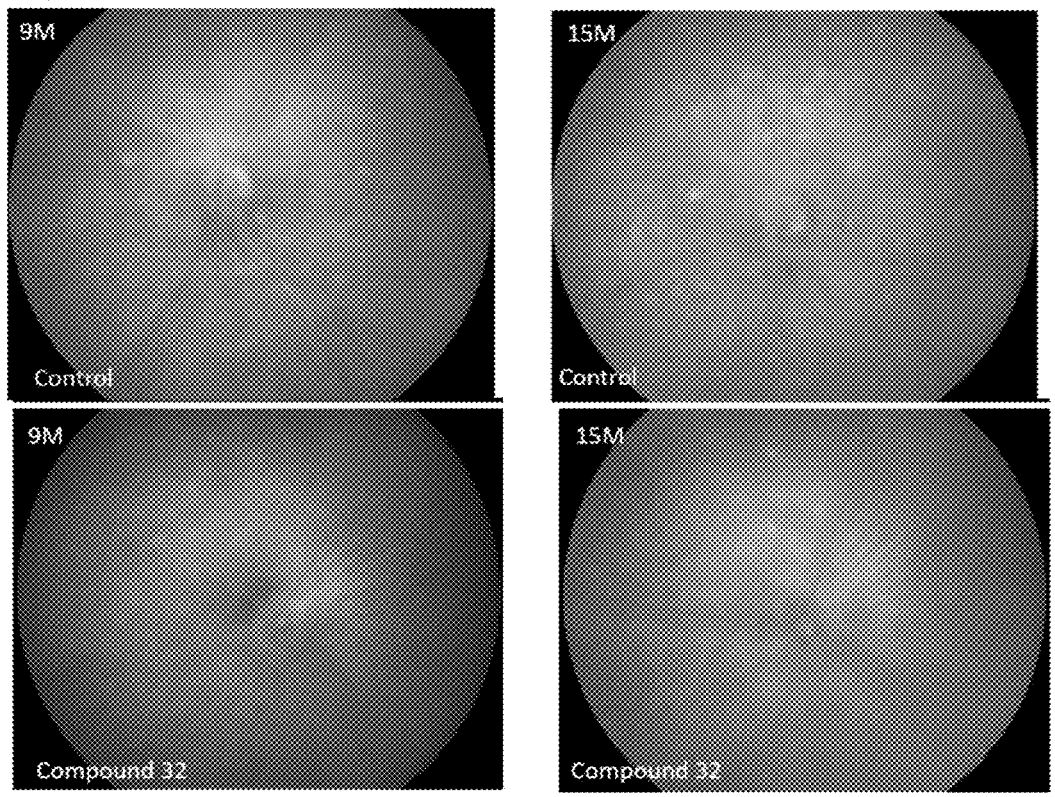
FIG. 2 shows fundus photographs of mice at the age of 9 and 15 months in Experiment 1. Upper panels: a control mouse. Lower panels: a mouse administered with Compound 32.
Figure 3:
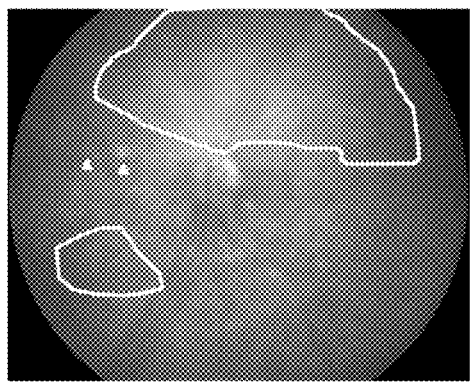
FIG. 3 corresponds to the upper panels of FIG. 2 (the control mouse) in which drusen are indicated with the arrow heads and the areas where increase of the drusen is observed are bounded by the lines.
Figure 3:
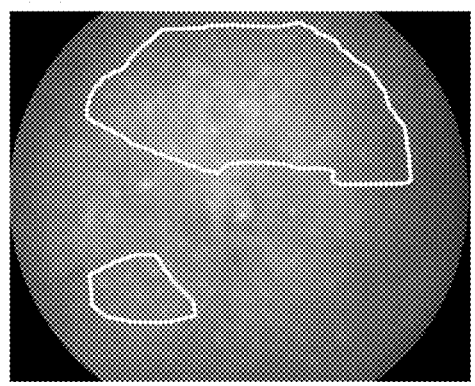
Figure 4:
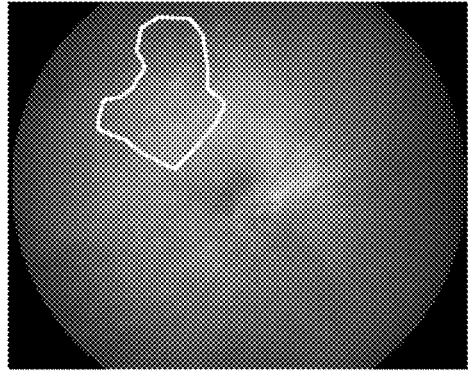
FIG. 4 corresponds to the lower panels of FIG. 2 (the mouse administered wish Compound 32) in which the area where disappearance of the drusen is observed is bounded by the line.
Figure 4:
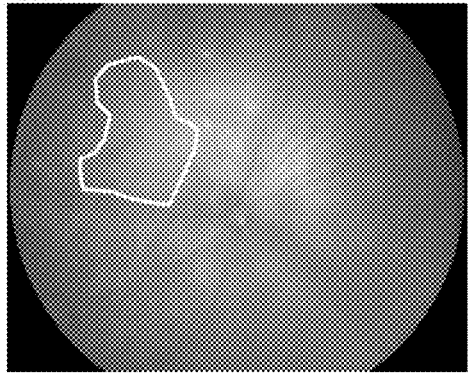
Figure 5:
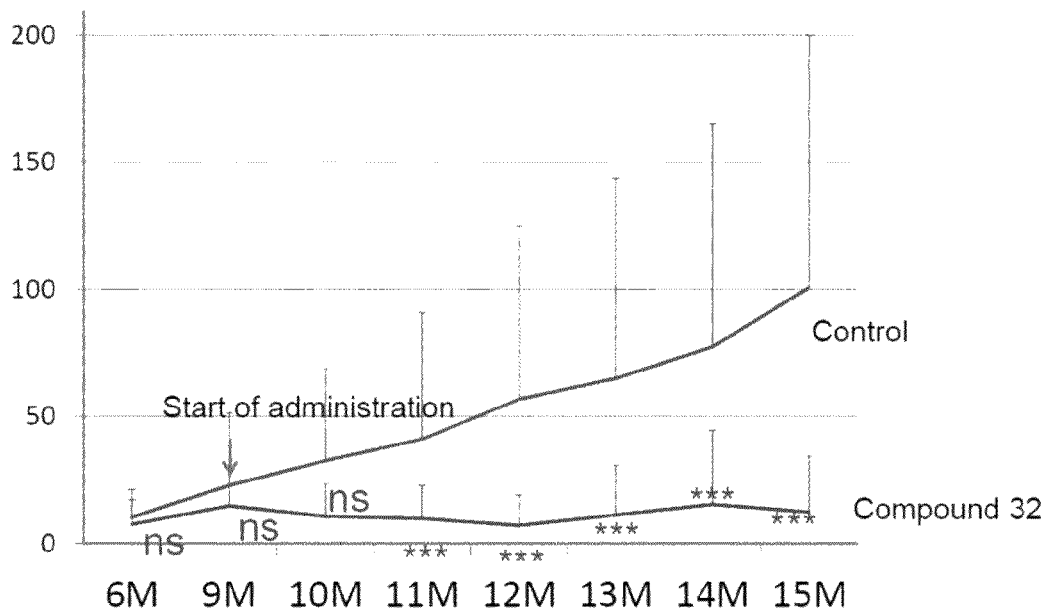
FIG. 5 is a graph showing the change of the number of the drusen in the mice of the group administered with Compound 32 and in the control group in Experiment 1. At the age of 6, 9, 10, 11, 12, 13, 14, and 15 months, in the group administered with Compound 32, n (number of eyes)=30, 29, 29, 29, 26, 24, 24, and 24, respectively, and in the control group, n=48, 45, 22, 21, 18, 18, 16, and 16, respectively. The abbreviation "ns" indicates no significant difference. The symbol "***" indicates significant difference ($p = <0.001$).
Figure 6:
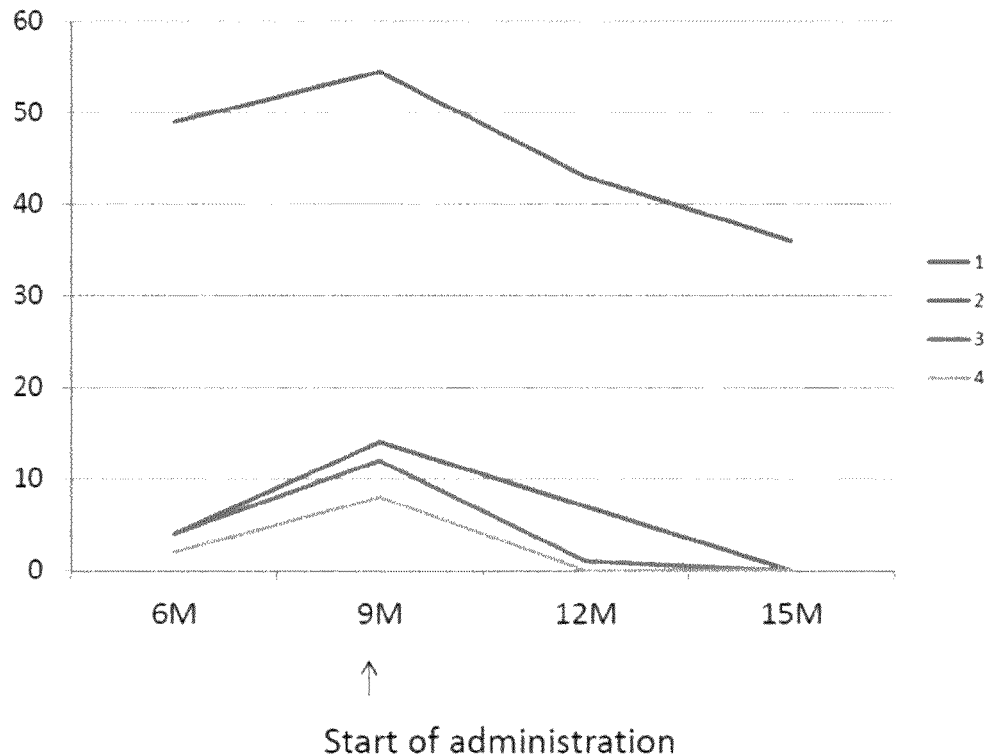
FIG. 6 individually shows time-dependent change of the number of the drusen in mice 1 to 4 administered with Compound 32 in Experiment 1.
Figure 7:
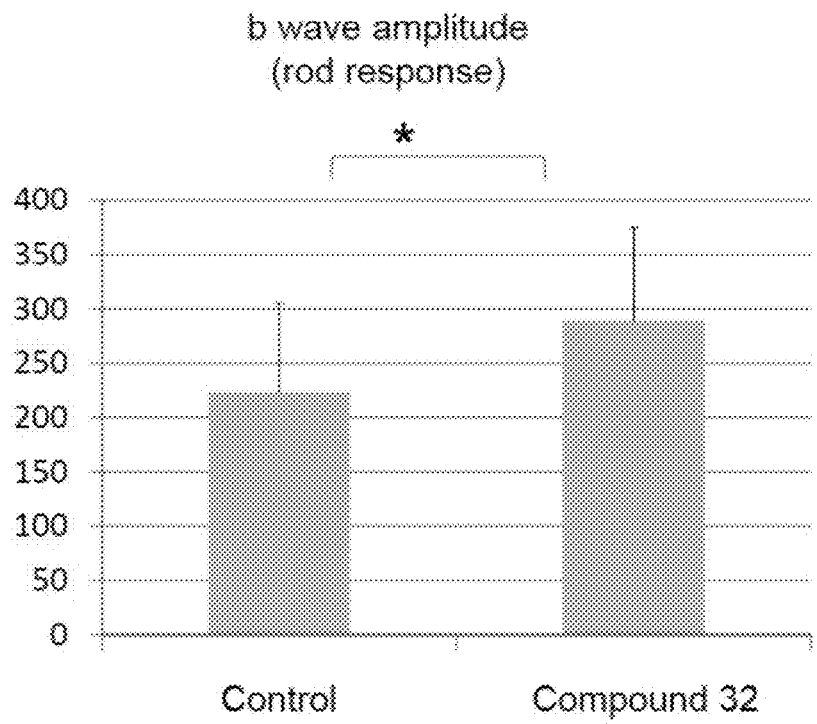
FIG. 7 shows b-wave amplitudes in the electroretinogram of the mice at the age of 15 months in the control group and the group administered with Compound 32 in Experiment 1. The symbol "*" indicates significant difference ($p = <0.05$).

FIGS. 2 to 4 show the fundus photographs at the age of 9 and 15 months. The white dot-like structures are the drusen. In the control mouse, the drusen increased in the areas bounded by the lines in FIG. 3. In the mouse administered with Compound 32, the drusen disappeared in the area bounded by the line in FIG. 4. The graph shown in FIG. 5 represents the numbers of the drusen found in the fundus photographs. The graph indicates that the drusen were gradually increased in the control group but not in the mice administered with Compound 32. FIG. 6 shows the time-dependent change of the numbers of the drusen in individual mice. The drusen increased until the age of nine months, when the administration started, then gradually decreased after the administration. FIG. 7 shows b-wave amplitudes in the electroretinogram of the mice in the control group and the group administered with Compound 32. The result indicates that retinal function is better in the mice administered with Compound 32 than in the control mice.

These results indicate that Compound 32 is capable of removing drusen and preventing impairment of retinal function in aged mice.

Example 3

Experiment 2: Suppression of Formation of Drusen in Young Mice

Figure 8:
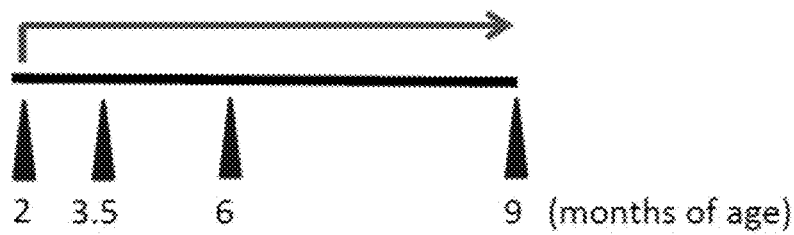
FIG. 8 shows scheme of Experiment 2.

The effect of the compound of number 32 (Compound 32) to suppress the formation of the drusen in young mice was tested. CCR2 deficient mice were used. The mice were allowed to freely drink water containing 0.385 mg/ml of Compound 32 from the age of two months. The mice in the control group were allowed to freely drink water not con-taining Compound 32. At the age of 2, 3.5, 6, and 9 months, the mice were examined by fundus photographs, OCT, and ERG. FIG. 8 shows the scheme of Experiment 2.

Figure 9:
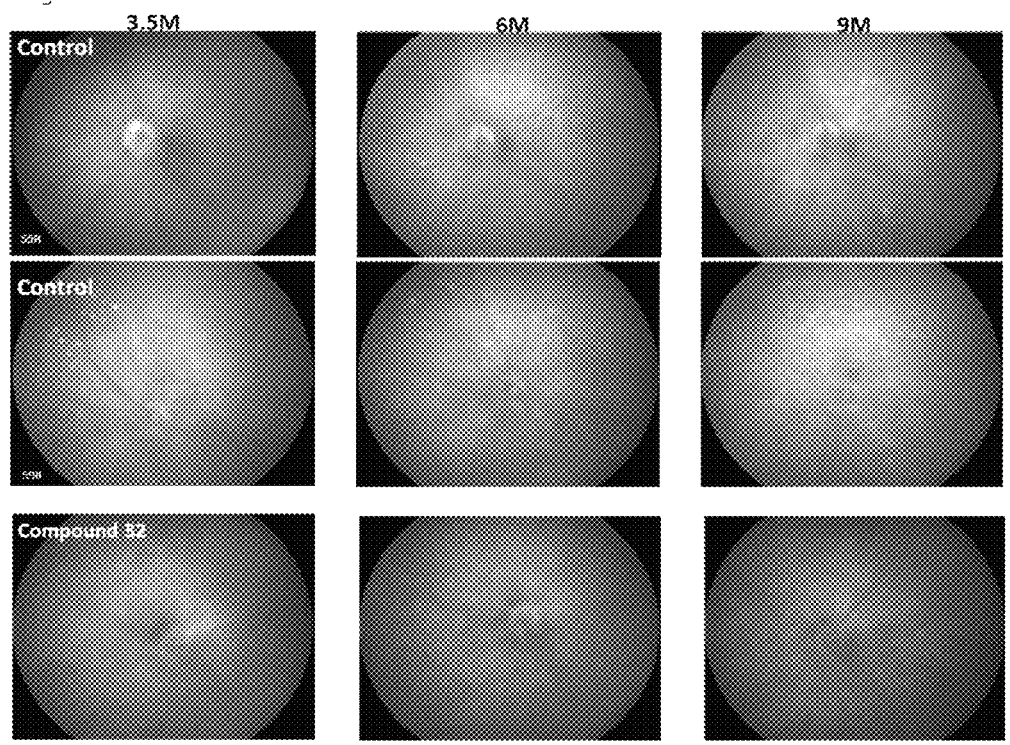
FIG. 9 shows fundus photographs of mice at the age of 3.5, 6, and 15 months in Experiment 2. Upper and middle panels: control mice. Lower panels: a mouse administered with Compound 32.
Figure 10:
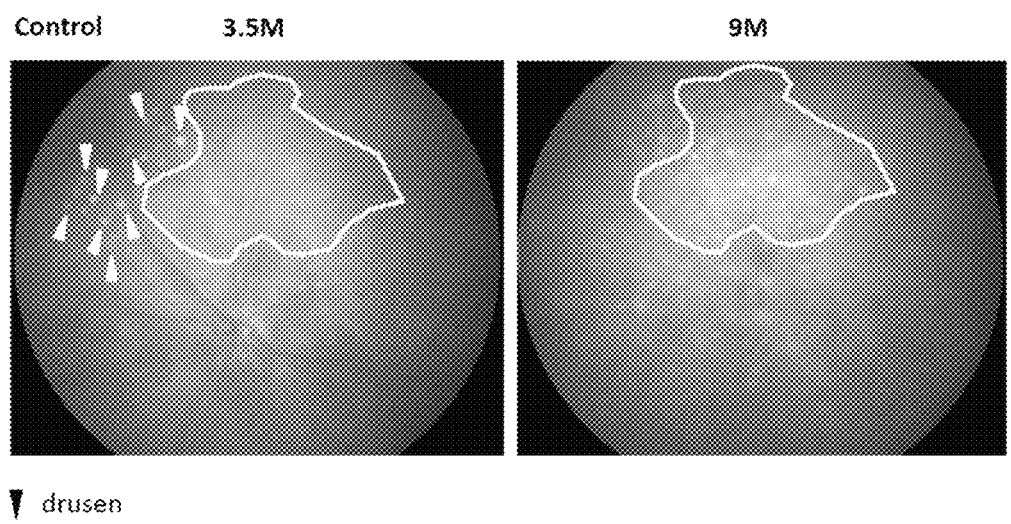
FIG. 10 corresponds to the fundus photographs of mice at the age of 3.5 and 15 months shown in the middle panels of FIG. 9 (the control mouse) in which the drusen are indicated with the arrow heads and the area where increase of the drusen is observed is bounded by the line.
Figure 11:
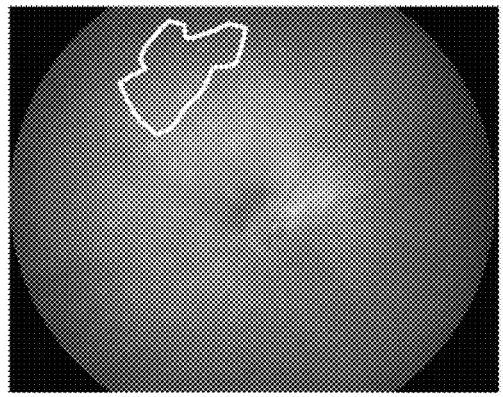
FIG. 11 corresponds to the fundus photographs of mice at the age of 3.5 and 15 months shown in the lower panels of FIG. 9 (the mouse administered with Compound 32) in which the area where disappearance of drusen is observed is bounded by the line.
Figure 11:
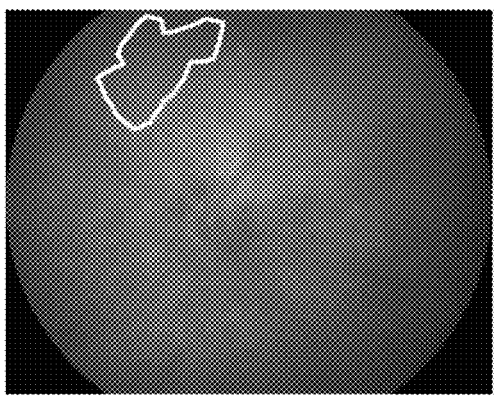
Figure 12:
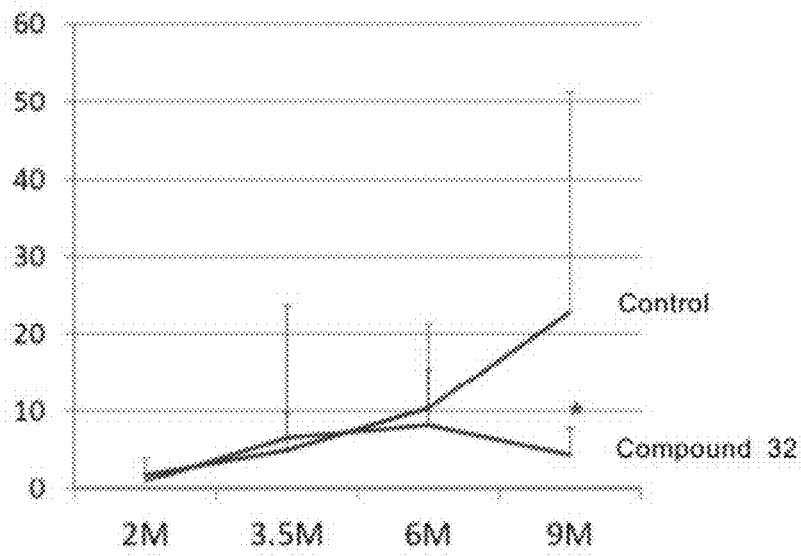
FIG. 12 is a graph showing the change of the number of the drusen in the mice of the group administered with Compound 32 and in the control group in Experiment 2. At the age of 2, 3.5, 6, and 9 months, in the group administered with Compound 32, n (number of eyes)=30, 22, 17, and 17, respectively, and in the control group, n=48, 52, 48, and 43, respectively. The symbol "*" indicates significant difference ($p = <0.05$).
Figure 13:
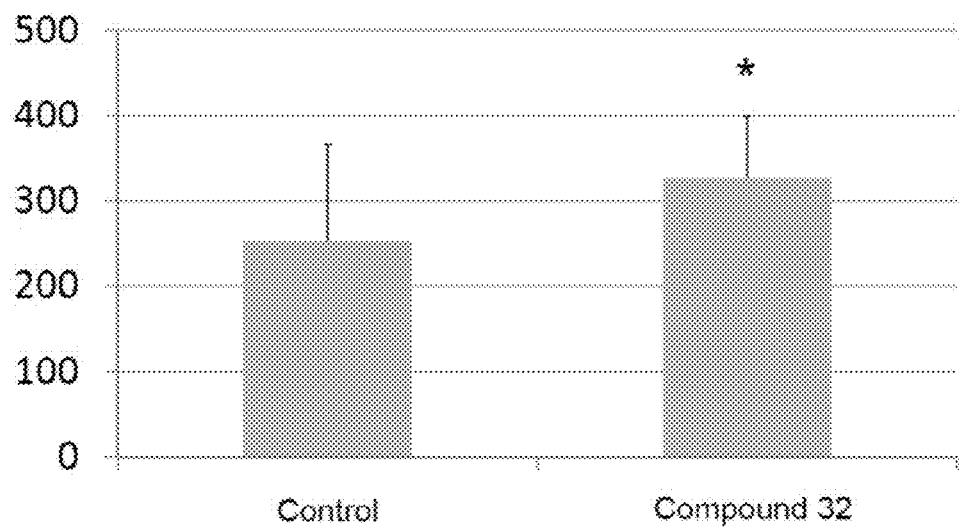
FIG. 13 shows b-wave amplitudes in the electroretinogram of the mice at the age of 9 months in the control group and the group administered with Compound 32 in Experiment 2. The symbol "*" indicates significant difference ($p = <0.05$).
Figure 14:
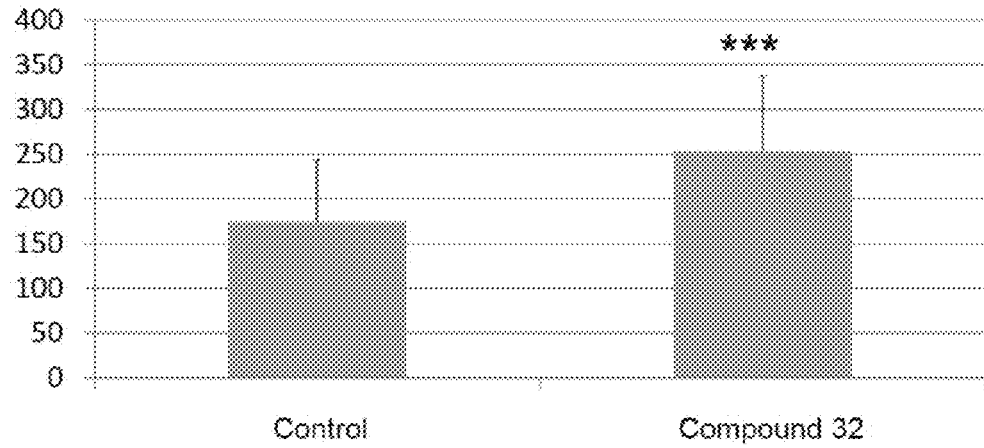
FIG. 14 shows a-wave amplitudes in the electroretinogram of the mice at the age of 9 months in the control group and the group administered with Compound 32 in Experiment 2. The symbol "***" indicates significant difference ($p = <0.001$).

FIGS. 9 to 11 show the fundus photographs at the age of 3.5, 6, and 9 months. The white dot-like structures are the drusen. In the control mouse, remarkable increase of the drusen is observed in the area bounded by the line in FIG. 10. In the mouse administered with Compound 32, the drusen did not increase. Remarkable suppression of the formation of the drusen is observed particularly in the area bounded by the line in FIG. 11. The graph shown in FIG. 12 represents the number of the drusen found in the fundus photographs. The graph indicates that the drusen were gradually increased in the control group but not in the mice administered with Compound 32. FIG. 13 shows b-wave amplitudes in the electroretinogram of the mice in the control group and the group administered with Compound 32. The result indicates that retinal function is better in the mice administered with Compound 32 than in the control mice. FIG. 14 shows a-wave amplitudes in the electroretinogram of the mice in the control group and the group administered with Compound 32. The result indicates that function of photoreceptor cells is better in the mice administered with Compound 32 than in the control mice.

These results indicate than Compound 32 is capable of suppressing formation of drusen and protecting retinal function in mice.

INDUSTRIAL APPLICABILITY

The results of the pharmacological tests demonstrate that the compounds of the present invention, particularly Compound 32 are capable of removing drusen and suppressing formation of drusen and thus useful for the prevention and treatment of age-related macular degeneration. Additionally, the compounds of the present invention are advantageous since they are effective via an oral route and thus can be easily administered.

The invention claimed is:

1. A method of removing drusen, suppressing formation of drusen, and/or treating age-related macular degeneration in a subject having drusen, comprising administering to the subject having drusen a therapeutically effective amount of a compound of formula (I):

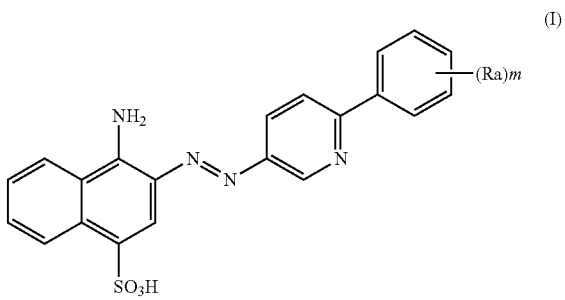

wherein
Ra is independently selected from the group consisting of halo, hydroxy, alkyl, halo-substituted alkyl, aryl, halo- or alkyl-substituted aryl, alkoxy, hydroxy- or carboxy-substituted alkoxy, aryloxy, halo- or alkyl-substituted aryloxy, CHO, C(O)-alkyl, C(O)-aryl, C(O)-alkyl-carboxyl, C(O)-alkylene-carboxy ester and cyano, and m is an integer selected from 0 to 4, or an oxide, ester, pharmaceutically acceptable salt or solvate thereof.

2. The method according to claim 1, wherein Ra is independently selected from the group consisting of halo, hydroxy, alkyl, halo-substituted alkyl and alkoxy.

3. The method according to claim 1, wherein Ra is independently selected from the group consisting of halo and alkyl.

4. The method according to claim 1, wherein the compound has two Ra groups, one of the Ra group is halo and the other is alkyl.

5. The method according to claim 1, wherein the compound is a compound of formula

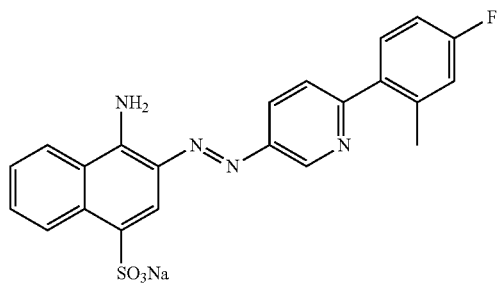

or an oxide, ester, pharmaceutically acceptable salt or solvate thereof.

6. The method according to claim 1, wherein the method removes the drusen and/or suppresses the formation of drusen.

7. The method according to claim 1, wherein the method treats the age-related macular degeneration.

8. The method according to claim 7, wherein the age-related macular degeneration is exudative age-related macular degeneration.

9. The method according to claim 7, wherein the age-related macular degeneration is atrophic age-related macular degeneration.

10. The method according to claim 1, wherein the compound of formula (I) or the oxide, ester, pharmaceutically acceptable salt or solvate thereof is administered orally.

11. A method of removing drusen, suppressing formation of drusen, and/or treating age-related macular in a patient having age-related macular degeneration, comprising administering to the patient having age-related macular degeneration a therapeutically effective amount of a compound of formula (I):

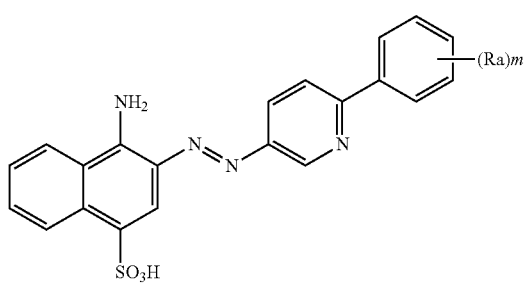

wherein

Ra is independently selected from the group consisting of halo, hydroxy, alkyl, halo-substituted alkyl, aryl, halo- or alkyl-substituted aryl, alkoxy, hydroxy- or carboxy-substituted alkoxy, aryloxy, halo- or alkyl-substituted aryloxy, CHO, C(O)-alkyl, C(O)-aryl, C(O)-alkyl-carboxyl, C(O)-alkylene-carboxy ester and cyano, and m is an integer selected from 0 to 4, or an oxide, ester, pharmaceutically acceptable salt or solvate thereof.

12. The method according to claim 11, wherein Ra is independently selected from the group consisting of halo, hydroxy, alkyl, halo-substituted alkyl and alkoxy.

13. The method according to claim 11, wherein Ra is independently selected from the group consisting of halo and alkyl.

14. The method according to claim 11, wherein the compound has two Ra groups, one of the Ra group is halo, and the other is alkyl.

15. The method according to claim 11, wherein the compound is a compound of formula

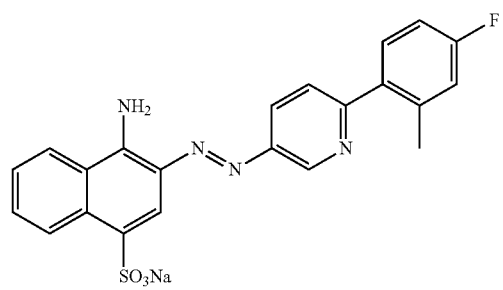

or an oxide, ester, pharmaceutically acceptable salt or solvate thereof.

16. The method according to claim 11, wherein the age-related macular degeneration is exudative age-related macular degeneration.

17. The method according to claim 11, wherein the age-related macular degeneration is atrophic age-related macular degeneration.

18. The method according to claim 11, wherein the compound is selected from the group consisting of 4-amino-3-(6-phenylpyridine-3-ylazo)naphthalene-1-sulfonic acid, 4-amino-3-(6-p-tolylpyridine-3-ylazo)naphthalene-1-sulfonic acid, 4-amino-3-(6-m-tolylpyridine-3-ylazo)naphthalene-1-sulfonic acid, 4-amino-3-(6-o-tolylpyridine-3-ylazo) naphthalene-1-sulfonic acid, 4-amino-3-(6-biphenyl-2-ylpyridine-3-ylazo)naphthalene-1-sulfonic acid, 3-[6-(2-acetylphenyl)pyridine-3-ylazo]-4-aminonaphthalene-1-sulfonic acid, 3-[6-(3-acetylphenyl)pyridine-3-ylazo]-4-aminonaphthalene-1-sulfonic acid, 3-[6-(4-acetylphenyl) pyridine-3-ylazo]-4-aminonaphthalenesulfonic acid, 4-amino-3-[6-(2,4-dichlorophenyl)pyridine-3-ylazo]naphthalene-1-sulfonic acid, 4-amino-3-[6-(2-trifluoromethylphenyl)pyridine-3-ylazo]naphthalene-1-sulfonic acid, 4-amino-3-[6-(4-trifluoromethylphenyl)pyridine-3-ylazo] naphthalene-1-sulfonic acid, 4-amino-3-[6-(2-chlorophenyl) pyridine-3-ylazo]naphthalene-1-sulfonic acid, 4-amino-3-[6-(3-chlorophenyl)pyridine-3-ylazo]naphthalene-1-sulfonic acid, 4-amino-3-[6-(4-chlorophenyl)pyridine-3-ylazo]naphthalene-1-sulfonic acid, 4-amino-3-[6-(2-methoxyphenyl)pyridine-3-ylazo]naphthalene-1-sulfonic acid, 4-amino-3-[6-(4-methoxyphenyl)pyridine-3-ylazo] naphthalene-1-sulfonic acid, 4-amino-3-[6-(2-isopropoxyphenyl)pyridine-3-ylazo]naphthalene-1-sulfonic acid, 4-amino-3-[6-(4-isopropoxyphenyl)pyridine-3-ylazo]naphthalene-1-sulfonic acid, 4-amino-3-[6-(2-phenoxyphenyl)pyridine-3-ylazo]naphthalene-1-sulfonic acid, 4-amino-3-[6-(3-methoxyphenyl)pyridine-3-ylazo]naphthalene-1-sulfonic acid, 4-amino-3-[6-(2,3-dimethylphenyl)pyridine-3-ylazo]naphthalene-1-sulfonic acid, 4-amino-3-[6-(2,5-dimethylphenyl)pyridine-3-ylazo]naphthalene-1-sulfonic acid, 4-amino-3-[6-(3,5-dimethylphenyl)pyridine-3-ylazo]naphthalene-1-sulfonic acid, 4-amino-3-[6-(3-trifluoromethylphenyl)pyridine-3-ylazo]naphthalene-1-sulfonic acid, methyl 4-{4-[5-(1-amino-4-sulfonaphthalene-2-ylazo)pyridine-2-yl]phenyl}-4-oxobutyrate, 4-amino-3-(6-biphenyl-3-ylpyridine-3-ylazo)naphthalene-1-sulfonic acid, 4-amino-3-[6-(3-cyanophenyl)pyridine-3-ylazo]naphthalene-1-sulfonic acid, 4-amino-3-[6-(4-cyanophenyl)pyridine-3-ylazo]naphthalene-1-sulfonic acid, 4-amino-3-[6-(3,5-bistrifluoromethylphenyl)pyridine-3-ylazo]naphthalenesulfonic acid, 4-amino-3-[6-(4-benzoylphenyl)pyridine-3-ylazo]naphthalene-1-sulfonic acid, 4-amino-3-[6-(2-propoxyphenyl)pyridine-3-ylazo]naphthalene-1-sulfonic acid, 4-amino-3-[6-(4-fluoro-2-methylphenyl)pyridine-3-ylazo]naphthalene-1-sulfonic acid, 4-amino-3-[6-(5-fluoro-2-propoxyphenyl)pyridine-3-ylazo]naphthalene-1-sulfonic acid, 4-amino-3-[6-(2-fluoro-6-propoxyphenyl)pyridine-3-ylazo]naphthalene-1-sulfonic acid, 4-amino-3-[6-(4-fluoro-2-propoxyphenyl)pyridine-3-ylazo]naphthalene-1-sulfonic acid, 4-amino-3-[6-(5-fluoro-2-methylphenyl)pyridine-3-ylazo]naphthalene-1-sulfonic acid, 4-amino-3-[6-(2-fluoro-5-methylphenyl)pyridine-3-ylazo]naphthalene-1-sulfonic acid, 4-amino-3-[6-(2-butoxyphenyl)pyridine-3-ylazo]naphthalene-1-sulfonic acid, 4-amino-3-[6-(2-hexyloxyphenyl)pyridine-3-ylazo]naphthalene-1-sulfonic acid, 4-amino-3-[6-(4-butylphenyl)pyridine-3-ylazo]naphthalene-1-sulfonic acid, 4-amino-3-[6-(2-hydroxyphenyl)pyridine-3-ylazo]naphthalene-1-sulfonic acid, 4-amino-3-{6-[2-(6-hydroxyhexyloxy)phenyl]pyridine-3-ylazo}naphthalene-1-sulfonic acid, 4-{2-[5-(1-amino-4-sulfonaphthalene-2-ylazo)pyridine-2-yl]phenoxy}butyric acid, 4-amino-3-[6-[2-(3-hydroxypropoxy)phenyl]pyridine-3-ylazo]naphthalene-1-sulfonic acid, 4-amino-3-[6-(2-isobutoxyphenyl)pyridine-3-ylazo]naphthalene-1-sulfonic acid, 4-amino-3-[6-(5-chloro-2-hydroxyphenyl)pyridine-3-ylazo]naphthalene-1-sulfonic acid, 4-amino-3-[6-(4-methylbiphenyl-2-yl)pyridine-3-ylazo]naphthalene-1-sulfonic acid, 4-amino-3-[6-(4'-chloro-4-methylbiphenyl-2-yl)pyridine-3-ylazo]naphthalene-1-sulfonic acid, 4-amino-3-[6-(4,3',5'-trimethylbiphenyl-2-yl)pyridine-3-ylazo]naphthalene-1-sulfonic acid, 4-amino-3-[6-(3'-chloro-4-methylbiphenyl-2-yl)pyridine-3-ylazo]naphthalene-1-sulfonic acid, 4-amino-3-[6-(2,6-dimethylphenyl)pyridine-3-ylazo]naphthalene-1-sulfonic acid, 4-amino-3-[6-(3-formyl-2-isopropoxy-5-methylphenyl)pyridine-3-ylazo]naphthalene-1-sulfonic acid, and 4-amino-3-[6-(3-formyl-2-butoxy-5-methylphenyl)pyridine-3-ylazo]naphthalene-1-sulfonic acid.

19. The method according to claim 11, wherein the compound is selected from the group consisting of 4-amino-3-(6-phenylpyridine-3-ylazo)naphthalene-1-sulfonic acid, 4-amino-3-(6-p-tolylpyridine-3-ylazo)naphthalene-1-sulfonic acid, 4-amino-3-(6-m-tolylpyridine-3-ylazo)naphthalene-1-sulfonic acid, 4-amino-3-(6-o-tolylpyridine-3-ylazo)naphthalene-1-sulfonic acid, 4-amino-3-(6-biphenyl-2-ylpyridine-3-ylazo)naphthalene-1-sulfonic acid, 3-[6-(2-acetylphenyl)pyridine-3-ylazo]-4-aminonaphthalene-1-sulfonic acid, 3-[6-(3-acetylphenyl)pyridine-3-ylazo]-4-aminonaphthalene-1-sulfonic acid, 3-[6-(4-acetylphenyl)pyridine-3-ylazo]-4-aminonaphthalenesulfonic acid, 4-amino-3-[6-(2,4-dichlorophenyl)pyridine-3-ylazo]naphthalene-1-sulfonic acid, 4-amino-3-[6-(2-trifluoromethylphenyl)pyridine-3-ylazo]naphthalene-1-sulfonic acid, 4-amino-3-[6-(4-trifluoromethylphenyl)pyridine-3-ylazo]naphthalene-1-sulfonic acid, 4-amino-3-[6-(2-chlorophenyl)pyridine-3-ylazo]naphthalene-1-sulfonic acid, 4-amino-3-[6-(3-chlorophenyl)pyridine-3-ylazo]naphthalene-1-sulfonic acid, 4-amino-3-[6-(4-chlorophenyl)pyridine-3-ylazo]naphthalene-1-sulfonic acid, 4-amino-3-[6-(2-methoxyphenyl)pyridine-3-ylazo]naphthalene-1-sulfonic acid, 4-amino-3-[6-(4-methoxyphenyl)pyridine-3-ylazo]naphthalene-1-sulfonic acid, 4-amino-3-[6-(2-isopropoxyphenyl)pyridine-3-ylazo]naphthalene-1-sulfonic acid, 4-amino-3-[6-(4-isopropoxyphenyl)pyridine-3-ylazo]naphthalene-1-sulfonic acid, 4-amino-3-[6-(2-phenoxyphenyl)pyridine-3-ylazo]naphthalene-1-sulfonic acid, 4-amino-3-[6-(3-methoxyphenyl)pyridine-3-ylazo]naphthalene-1-sulfonic acid, 4-amino-3-[6-(2,3-dimethylphenyl)pyridine-3-ylazo]naphthalene-1-sulfonic acid, 4-amino-3-[6-(2,5-dimethylphenyl)pyridine-3-ylazo]naphthalene-1-sulfonic acid, 4-amino-3-[6-(3,5-dimethylphenyl)pyridine-3-ylazo]naphthalene-1-sulfonic acid, 4-amino-3-[6-(3-trifluoromethylphenyl)pyridine-3-ylazo]naphthalene-1-sulfonic acid, methyl 4-{4-[5-(1-amino-4-sulfonaphthalene-2-ylazo)pyridine-2-yl]phenyl}-4-oxobutyrate, 4-amino-3-(6-biphenyl-3-ylpyridine-3-ylazo)naphthalene-1-sulfonic acid, 4-amino-3-[6-(3-cyanophenyl)pyridine-3-ylazo]naphthalene-1-sulfonic acid, 4-amino-3-[6-(4-cyanophenyl)pyridine-3-ylazo]naphthalene-1-sulfonic acid, 4-amino-3-[6-(3,5-bistrifluoromethylphenyl)pyridine-3-ylazo]naphthalenesulfonic acid, 4-amino-3-[6-(4-benzoylphenyl)pyridine-3-ylazo]naphthalene-1-sulfonic acid, 4-amino-3-[6-(2-propoxyphenyl)pyridine-3-ylazo]naphthalene-1-sulfonic acid, 4-amino-3-[6-(4-fluoro-2-methylphenyl)pyridine-3-ylazo]naphthalene-1-sulfonic acid, 4-amino-3-[6-(5-fluoro-2-propoxyphenyl)pyridine-3-ylazo]naphthalene-1-sulfonic acid, 4-amino-3-[6-(2-fluoro-6-propoxyphenyl)pyridine-3-ylazo]naphthalene-1-sulfonic acid, 4-amino-3-[6-(4-fluoro-2-propoxyphenyl)pyridine-3-ylazo]naphthalene-1-sulfonic acid, 4-amino-3-[6-(5-fluoro-2-methylphenyl)pyridine-3-ylazo]naphthalene-1-sulfonic acid, 4-amino-3-[6-(2-fluoro-5-methylphenyl)pyridine-3-ylazo]naphthalene-1-sulfonic acid, 4-amino-3-[6-(2-butoxyphenyl)pyridine-3-ylazo]naphthalene-1-sulfonic acid, 4-amino-3-[6-(2-hexyloxyphenyl)pyridine-3-ylazo]naphthalene-1-sulfonic acid, 4-amino-3-[6-(4-butylphenyl)pyridine-3-ylazo]naphthalene-1-sulfonic acid, 4-amino-3-[6-(2-hydroxyphenyl)pyridine-3-ylazo]naphthalene-1-sulfonic acid, 4-amino-3-{6-[2-(6-hydroxyhexyloxy)phenyl]pyridine-3-ylazo}naphthalene-1-sulfonic acid, 4-{2-[5-(1-amino-4-sulfonaphthalene-2-ylazo)pyridine-2-yl]phenoxyl}butyric acid, 4-amino-3-[6-[2-(3-hydroxypropoxy)phenyl]pyridine-3-ylazo]naphthalene-1-sulfonic acid, 4-amino-3-[6-(2-isobutoxyphenyl)pyridine-3-ylazo]naphthalene-1-sulfonic acid, 4-amino-3-[6-(5-chloro-2-hydroxyphenyl)pyridine-3-ylazo]naphthalene-1-sulfonic acid, 4-amino-3-[6-(4-methylbiphenyl-2-yl)pyridine-3-ylazo]naphthalene-1-sulfonic acid, 4-amino-3-[6-(4'-chloro-4-methylbiphenyl-2-yl)pyridine-3-ylazo]naphthalene-1-sulfonic acid, 4-amino-3-[6-(4,3',5'-trimethylbiphenyl-2-yl)pyridine-3-ylazo]naphthalene-1-sulfonic acid, 4-amino-3-[6-(3'-chloro-4-methylbiphenyl-2-yl)pyridine-3-ylazo]naphthalene-1-sulfonic acid, 4-amino-3-[6-(2,6-dimethylphenyl)pyridine-3-ylazo]naphthalene-1-sulfonic acid, 4-amino-3-[6-(3-formyl-2-isopropoxy-5-methylphenyl)pyridine-3-ylazo]naphthalene-1-sulfonic acid, and 4-amino-3-[6-(3-formyl-2-butoxy-5-methylphenyl)pyridine-3-ylazo]naphthalene-1-sulfonic acid.

20. A method of removing drusen and/or treating age-related macular degeneration in a subject in need thereof, comprising administering to the subject a therapeutically effective amount of a compound of formula (I):

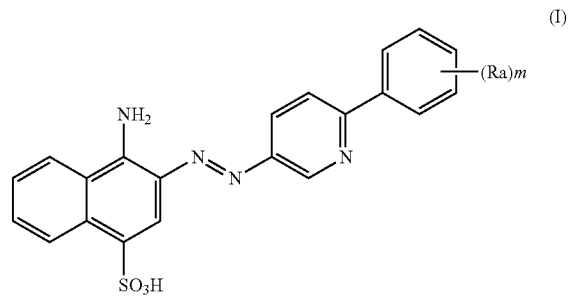

wherein

Ra is independently selected from the group consisting of halo, hydroxy, alkyl, halo-substituted alkyl, aryl, halo- or alkyl-substituted aryl, alkoxy, hydroxy- or carboxy-substituted alkoxy, aryloxy, halo- or alkyl-substituted aryloxy, CHO, C(O)-alkyl, C(O)-aryl, C(O)-alkyl-carboxyl, C(O)-alkylene-carboxy ester and cyano, and m is an integer selected from 0 to 4, or an oxide, ester, pharmaceutically acceptable salt or solvate thereof.

* * * * *